(12) United States Patent
Chen et al.

(10) Patent No.: US 11,219,483 B2
(45) Date of Patent: Jan. 11, 2022

(54) METHODS AND SYSTEMS FOR REAL-TIME PLANNING AND MONITORING OF ABLATION NEEDLE DEPLOYMENT IN TISSUE

(71) Applicant: Gynesonics Inc., Redwood City, CA (US)

(72) Inventors: Jiayu Chen, Palo Alto, CA (US); Hyeonsoo Chang, Palo Alto, CA (US); Edmond Ming Wai Chiu, San Francisco, CA (US); Amer Hammudi, Tracy, CA (US); Harry Kwan, San Francisco, CA (US); Michael A. Munrow, Belmont, CA (US)

(73) Assignee: Gynesonics Inc., Redwood City, CA (US)

( * ) Notice: Subject to any disclaimer, the term of this patent is extended or adjusted under 35 U.S.C. 154(b) by 821 days.

(21) Appl. No.: 15/811,520

(22) Filed: Nov. 13, 2017

(65) Prior Publication Data

US 2018/0132927 A1    May 17, 2018

Related U.S. Application Data

(60) Provisional application No. 62/421,669, filed on Nov. 14, 2016.

(51) Int. Cl.
*A61B 18/14* (2006.01)
*A61B 18/18* (2006.01)
(Continued)

(52) U.S. Cl.
CPC .......... *A61B 18/1477* (2013.01); *A61B 18/18* (2013.01); *A61B 18/1815* (2013.01);
(Continued)

(58) Field of Classification Search
CPC . A61B 18/18; A61B 18/1815; A61B 18/1477; A61B 18/02; A61B 90/37
See application file for complete search history.

(56) References Cited

U.S. PATENT DOCUMENTS

| | | | |
|---|---|---|---|
| 6,050,992 | A | 4/2000 | Nichols |
| 6,540,677 | B1 | 4/2003 | Angelsen et al. |

(Continued)

FOREIGN PATENT DOCUMENTS

| | | | |
|---|---|---|---|
| JP | H11508790 A | 8/1999 | |
| JP | 2001340350 A | 12/2001 | |

(Continued)

OTHER PUBLICATIONS

International Search Report and Written Opinion dated Jan. 17, 2018 for International PCT Patent Application No. PCT/US2017/061366.

(Continued)

*Primary Examiner* — Joanne M Hoffman
(74) *Attorney, Agent, or Firm* — Wilson Sonsini Goodrich & Rosati

(57) ABSTRACT

A control handle of a treatment probe is manipulated to advance and/or deploy one or more treatment structures into tissue. The treatment probe is coupled to a display to show an image field including target tissue for treatment. Virtual treatment and safety boundaries are overlaid over the image field. The boundaries include virtual stop positions for the needle and tines. A joystick or directional pad on the probe handle, operable independently from the user interface to advance and/or deploy the one or more treatment structures, can be manipulated to adjust the size and/or position of these boundaries. Sensors within the probe detect the real-time position of the one or more treatment structures, and the sensed positions are displayed in real-time. The user can (Continued)

observe the display to deploy the one or more treatment structures to the displayed virtual stop positions.

34 Claims, 14 Drawing Sheets

(51) Int. Cl.
*A61B 90/00* (2016.01)
*A61B 18/00* (2006.01)
*A61B 8/08* (2006.01)
*A61B 18/02* (2006.01)
*A61B 18/04* (2006.01)
*A61B 34/10* (2016.01)

(52) U.S. Cl.
CPC ............ *A61B 90/37* (2016.02); *A61B 8/0841* (2013.01); *A61B 18/02* (2013.01); *A61B 18/042* (2013.01); *A61B 34/10* (2016.02); *A61B 90/36* (2016.02); *A61B 2018/00208* (2013.01); *A61B 2018/00577* (2013.01); *A61B 2018/1425* (2013.01); *A61B 2018/1475* (2013.01); *A61B 2090/0811* (2016.02); *A61B 2090/363* (2016.02); *A61B 2090/378* (2016.02)

(56) References Cited

U.S. PATENT DOCUMENTS

| | | | |
|---|---|---|---|
| 6,623,481 B1 | 9/2003 | Garbagnati et al. | |
| 6,936,048 B2 | 8/2005 | Hurst | |
| 6,944,490 B1 | 9/2005 | Chow | |
| 6,969,354 B1 | 11/2005 | Marian | |
| 7,160,296 B2 | 1/2007 | Pearson et al. | |
| 7,229,401 B2 | 6/2007 | Kindlein | |
| 7,387,628 B1 | 6/2008 | Behl et al. | |
| 7,517,346 B2 | 4/2009 | Sloan et al. | |
| 7,815,571 B2 | 10/2010 | Gerbi et al. | |
| 7,874,986 B2 | 1/2011 | Deckman et al. | |
| 7,918,795 B2* | 4/2011 | Grossman | A61B 18/1477 600/439 |
| 7,963,941 B2 | 6/2011 | Wilk | |
| 8,080,009 B2 | 12/2011 | Lee et al. | |
| 8,088,072 B2* | 1/2012 | Munrow | A61B 18/1477 600/464 |
| 8,157,741 B2 | 4/2012 | Hirota | |
| 8,157,745 B2 | 4/2012 | Schoot | |
| 8,206,300 B2 | 6/2012 | Deckman et al. | |
| 8,216,231 B2 | 7/2012 | Behl et al. | |
| 8,221,321 B2 | 7/2012 | McMorrow et al. | |
| 8,262,574 B2 | 9/2012 | Placek et al. | |
| 8,262,577 B2 | 9/2012 | Munrow et al. | |
| 8,287,485 B2 | 10/2012 | Kimura et al. | |
| 8,377,041 B2 | 2/2013 | Frassica et al. | |
| 8,469,893 B2 | 6/2013 | Chiang et al. | |
| 8,512,330 B2 | 8/2013 | Epstein et al. | |
| 8,512,333 B2 | 8/2013 | Epstein et al. | |
| 8,540,634 B2 | 9/2013 | Bruce et al. | |
| 8,585,598 B2 | 11/2013 | Razzaque et al. | |
| 8,622,911 B2 | 1/2014 | Hossack et al. | |
| 8,663,130 B2 | 3/2014 | Neubach et al. | |
| 8,718,339 B2 | 5/2014 | Tonomura et al. | |
| 8,814,796 B2 | 8/2014 | Martin et al. | |
| 8,992,427 B2* | 3/2015 | Munrow | A61B 8/12 600/439 |
| 9,089,287 B2 | 7/2015 | Sliwa et al. | |
| 9,198,707 B2 | 12/2015 | McKay et al. | |
| 9,198,719 B2 | 12/2015 | Murdeshwar et al. | |
| 9,247,925 B2 | 2/2016 | Havel et al. | |
| 9,439,627 B2 | 9/2016 | Case et al. | |
| 9,510,898 B2 | 12/2016 | Epstein et al. | |
| 9,516,996 B2 | 12/2016 | Diolaiti et al. | |
| 9,861,336 B2* | 1/2018 | Munrow | A61B 18/1477 |
| 2007/0006215 A1 | 1/2007 | Epstein et al. | |
| 2007/0179380 A1 | 8/2007 | Grossman | |
| 2007/0249939 A1 | 10/2007 | Gerbi et al. | |
| 2008/0033493 A1* | 2/2008 | Deckman | A61B 18/0218 607/3 |
| 2008/0228081 A1 | 9/2008 | Becker et al. | |
| 2009/0043295 A1 | 2/2009 | Arnal et al. | |
| 2009/0099544 A1* | 4/2009 | Munrow | A61B 34/10 604/506 |
| 2009/0131790 A1* | 5/2009 | Munrow | A61B 8/4488 600/439 |
| 2009/0287081 A1* | 11/2009 | Grossman | A61B 8/12 600/439 |
| 2010/0056926 A1 | 3/2010 | Deckman et al. | |
| 2010/0262133 A1 | 10/2010 | Hoey et al. | |
| 2012/0035474 A1 | 2/2012 | Deckman et al. | |
| 2012/0071794 A1* | 3/2012 | Karni | A61B 34/30 601/2 |
| 2012/0165813 A1 | 6/2012 | Lee et al. | |
| 2012/0209115 A1 | 8/2012 | Tonomura | |
| 2012/0277737 A1 | 11/2012 | Curley | |
| 2012/0310236 A1 | 12/2012 | Placek et al. | |
| 2012/0316440 A1 | 12/2012 | Munrow et al. | |
| 2013/0137979 A1 | 5/2013 | Deckman et al. | |
| 2013/0281863 A1 | 10/2013 | Chiang et al. | |
| 2013/0317366 A1 | 11/2013 | Hirayama et al. | |
| 2014/0073910 A1* | 3/2014 | Munrow | A61B 5/066 600/424 |
| 2014/0180273 A1 | 6/2014 | Nair | |
| 2014/0276081 A1 | 9/2014 | Tegels | |
| 2015/0150497 A1 | 6/2015 | Goldchmit | |
| 2015/0173592 A1 | 6/2015 | Leeflang et al. | |
| 2015/0257779 A1 | 9/2015 | Sinelnikov et al. | |
| 2016/0113621 A1 | 4/2016 | Deckman et al. | |
| 2016/0151041 A1 | 6/2016 | Lee et al. | |
| 2016/0278740 A1 | 9/2016 | Negrila et al. | |
| 2016/0310042 A1 | 10/2016 | Kesten et al. | |

FOREIGN PATENT DOCUMENTS

| | | |
|---|---|---|
| JP | 2006513831 A | 4/2006 |
| JP | 2007215672 A | 8/2007 |
| WO | WO-2014039795 A1 | 3/2014 |
| WO | WO-2018089923 A1 | 5/2018 |

OTHER PUBLICATIONS

EP17870152.0 Extended European Search Report dated Sep. 30, 2019.

* cited by examiner

METHODS AND SYSTEMS FOR REAL-TIME PLANNING AND MONITORING OF ABLATION NEEDLE DEPLOYMENT IN TISSUE

CROSS-REFERENCE

This application claims the benefit of U.S. Provisional Application No. 62/421,669, filed Nov. 14, 2016, which application is incorporated herein by reference.

The subject matter of this application is related to that of U.S. patent application Ser. No. 12/245,567, filed on Oct. 3, 2008 and now issued as U.S. Pat. No. 8,088,072 on Jan. 3, 2012, Ser. No. 13/307,304, filed on Nov. 30, 2011 and now issued as U.S. Pat. No. 8,262,577 on Sep. 11, 2012, Ser. No. 13/589,975, filed on Aug. 20, 2012, Ser. No. 12/198,861, filed on Aug. 26, 2008, Ser. No. 13/023,383, filed on Feb. 8, 2011 and now issued as U.S. Pat. No. 8,206,300, Ser. No. 14/989,732, filed on Jan. 6, 2016, Ser. No. 13/484,076, filed on May 30, 2012, Ser. No. 12/712,969, filed on Feb. 25, 2010 and now issued as U.S. Pat. No. 8,262,574 on Sep. 11, 2012, Ser. No. 13/589,956, filed Aug. 20, 2012, Ser. No. 13/801,782, filed Mar. 13, 2013, and Ser. No. 13/801,840, filed Mar. 13, 2013 and now issued as U.S. Pat. No. 8,992,427, and U.S. Provisional Patent Application No. 62/421,119, filed on Nov. 11, 2016, the contents of which are fully incorporated by reference herein.

BACKGROUND

1. Field of the Invention

The present invention relates generally to medical methods and apparatus. More particularly, the present invention relates to methods and systems for controlling the deployment of needles using treatment and safety boundaries projected onto an image of tissue to be treated.

Current medical treatments of organs and tissues within a patient's body often use a needle or other elongate body for delivery of energy, therapeutic agents or the like. Optionally, the methods use ultrasound imaging to observe and identify a treatment target and track the position of the needle relative to the treatment target.

Of particular interest to the present invention, a treatment for uterine fibroids has recently been proposed which relies on the transvaginal or laparoscopic positioning of a treatment probe or device in the patient's uterus. A radiofrequency or other energy or therapeutic delivery needle is deployed from the device into the fibroid, and energy and/or therapeutic substances are delivered in order to ablate or treat the fibroid. To facilitate locating the fibroids and positioning the needles within the fibroids, the treatment device includes an ultrasonic imaging array with an adjustable field of view in a generally forward or lateral direction relative to an axial shaft which carries the needle. The needle is advanced from the shaft and across the field of view so that the needle can be visualized and directed into the tissue and the targeted fibroid.

While effective and very beneficial for patients, such needle ablation and treatment protocols face several challenges. First, initial deployment of the needle can be difficult, particularly for physicians who have less experience. While the physician can view the tissue and target anatomy in real time on an imaging screen, it can be difficult to precisely predict the path the needle will take and assess its final treatment position. While the needle can certainly be partially or fully retracted and redeployed, it would be advantageous to minimize the number of deployments required before treatment is effected.

Another challenge comes after the needle has been deployed. While the position of the needle can be observed on the ultrasonic or other visual image, the treatment volume resulting from energy or other therapeutic delivery can be difficult to predict. As with initial positioning, experience will help but it would be desirable to reduce the need to exercise judgment and conjecture.

U.S. Pat. No. 8,088,072, commonly assigned with the present application, describes a system for projecting safety and treatment boundaries on a real time image of the fibroid or other tissue structure to be treated. While very effective when used with single needles, the system of the '072 patent is not optimized for use with multiple needle/tine assemblies, such as those taught in commonly owned U.S. Pat. Nos. 8,206,300 and 8,262,574.

U.S. Pat. No. 8,992,427, commonly assigned with the present application, describes a system for implementing an ablation procedure by sliding and/or rotating a knob on the device handle. The operation of the control knob during a treatment procedure can be less than ideal in many cases. For example, the use of the control knob during the treatment procedure may be less intuitive than ideal for physicians who have less experience. In implementing the treatment, the user may often shift their attention from their observation of the display showing the imaging field and often the treatment and safety regions to the operation of the control handle.

For these reasons, it would be desirable to provide improved systems and methods for the deployment of energy delivery and other needles within ultrasonic or other imaging fields of view in energy delivery or other therapeutic protocols. It would be particularly useful to provide the treating physician with information which would assist in initial deployment of a plurality of needles or tines in order to improve the likelihood that the needle assembly will be properly positioned relative to a targeted anatomy to be treated. It would also be desirable to provide feedback to the physician to assist in accurately predicting a treatment volume. Such information should allow the physician, if necessary, to reposition the probe in order to increase the likelihood of fully treating the anatomy. Furthermore, it would be desirable to provide feedback to the physician allowing the physician to assess a safety margin so that sensitive tissue structures are not damaged. All such feedback or other information is preferably provided visually on the ultrasonic or other imaging screen so that the needle position can be quickly predicted, assessed, and treatment initiated. It would be further desirable if the feedback information were presented on a display screen in response to manipulating the probe while minimizing the need to enter data or commands onto a system controller or display, and still further desirable if such manipulation of the probe could set stops or other limits which controlled the extent of subsequent needle deployment. It would be further desirable to provide the treating physician with an intuitive control to manipulate the treatment probe in response to the feedback, and still further desirable to provide the treatment physician with a unitary control for both the system controller or display and the treatment probe. It would be further desirable to allow the treating physician to re-position a treatment probe already placed in a surgical field without completely withdrawing and re-inserting the treatment probe. At least some of these objectives will be met by the inventions described hereinafter.

2. Description of the Background Art

U.S. Pat. Nos. 8,992,427, 8,088,072; 8,206,300, and 8,262,574 have been described above and are incorporated herein by reference. U.S. Pat. No. 7,918,795, commonly assigned with the present application, describes probes useful for both imaging and treating uterine fibroids, which probes could be used in the systems and methods of the present application and is incorporated herein by reference. Other commonly assigned patents and published applications describing probes useful for treating uterine fibroids in the systems include U.S. Pat. Nos. 7,874,986 and 7,815,571; and U.S. Patent Publications 2007/0179380 and 2008/0033493. See also U.S. Pat. No. 6,050,992 and U.S. Patent Publication 2007/0006215.

SUMMARY

The present invention provides methods and systems for deploying needle structures in tissue. The needle structures may in some cases comprise a single needle but in most cases will comprise multiple needles or needle and tine assemblies as described in more detail below. The needle structures are usually intended to deliver a therapy to the tissue, most typically being configured to deliver radiofrequency energy, plasma energy, therapeutic ultrasound energy, microwave energy, heat, cold (cryogenic treatment), or other energy to ablate or otherwise modify a target tissue or targeted anatomy within the tissue. Alternatively or in combination, the needle structures could also provide drug or other substance delivery, morcellation, or other tissue treatments which can be effected using a needle structure.

The methods and systems of the present invention may be particularly suitable for treating fibroids in a patient's uterus where a treatment probe carrying the needle structure and an imaging transducer, typically an ultrasonic imaging transducer, is introduced transvaginally and transcervically into the uterus, or in other cases laparoscopically into and through an exterior of the uterus or other organ or tissue target. The treatment probe may be manipulated within the uterus to deliver ablative energy to the fibroid as described in more detail below. In most embodiments of the present invention, the needle structure is "virtually" deployed on a real-time image of the tissue prior to actual deployment of the needle in the actual tissue. Treatment and/or safety boundaries within the tissue will also be determined and optionally adjusted prior to and/or during the actual deployment of the needle structure. In many embodiments, the actual position of the needle structure may be tracked and the corresponding treatment and/or safety boundaries may be projected on the screen in real time. In many embodiments, both the deployment of the needle structure and adjustment of the displayed treatment and/or safety boundaries are controlled with a handle of the treatment probe. The treatment and safety boundaries can be checked before treatment is commenced.

The methods and systems of the present invention may further provide that, once the parameters of the virtual deployment have been selected using the virtual images, the needle structure can actually be deployed in the real tissue at a location and/or in a pattern which matches the virtual deployment configuration. This system may track the position of the treatment probe and/or needle structure in the uterus, thus allowing treatment and safety boundaries which may be projected upon the real-time image of the tissue to be calculated and/or updated as the treatment probe is moved and the needle structure advanced by the treating physician. One or more controls elements on the treatment probe handle may be manipulated to move, translate, enlarge, shrink, or otherwise adjust or re-position the treatment and safety boundaries displayed. In many embodiments, the one or more control elements may be manipulated to establish one or more "stop" positions corresponding to the user-desired limits to needle deployment and/or to a user-defined deployment pattern, which will typically be within the treatment and safety boundaries. The treatment and safety boundaries may be calculated by the system based on the user-defined "stop" positions as well as on energy delivery data which may be supplied to or generated by a system controller. Once the treatment region and/or safety boundary are properly established and positioned on the real-time image relative to the anatomy to be treated, the physician may hold the treatment probe in place and use the control handle to deploy the needle structure until it reaches its "stop" position(s) which have typically been preset into the treatment probe during the initial imaging and set-up phase of the treatment. In some cases, the stops can be automatically set as the physician manipulates the treatment and/or safety boundary on the screen using the controls on the treatment probe. In alternative embodiments, the physician may manipulate the treatment probe and advance the needle structure while viewing the safety and/or treatment boundaries in real time without having previewed the virtual projections.

In the exemplary embodiments, at least one main or central needle will be deployed from the treatment probe, and a plurality of tines or secondary needles will be deployed from the main or central needle(s). Most often, there will be a single main needle which is deployed distally from a shaft of the treatment probe along a central axis thereof. A plurality of tines may then be advanced from the single needle in a distally diverging pattern. In other embodiments, a plurality of needles or tines may be advanced from the treatment probe without use of a main or central needle. In such cases, the needles or tines will typically expand or diverge into a three-dimensional array as they are advanced distally.

Exemplary anatomical features that may be imaged and subsequently treated include fibroids, tumors, encapsulated tissue masses, pseudo-encapsulated tissue masses, and the like. Of particular interest of the present invention, the treatment probe may be positioned in the uterus and the needle structure deployed to a location proximate to or within a fibroid located in the myometrium tissue of the uterus. In such cases, it will be desirable to also image the serosa which surrounds the myometrium and/or other sensitive anatomical features that could be damaged by the energy-mediated treatments described herein.

As used herein, a treatment region is defined by a treatment boundary which is calculated by the system controller or established by the user based upon the needle structure deployment configuration (either as set by the virtual "stops" or as calculated in real-time as the needle structure is deployed) and the energy delivery parameters set by or input into the system controller. Energy or other therapy delivered by the needle structure deployed in the selected pattern at the selected location will effectively treat the target tissue to achieve ablation or other therapeutic results. As described below, it will thus be desirable to manipulate the treatment probe as well as the needle structure stop(s) and/or actual needle structure so that the treatment region at least partially surrounds the anatomy to be treated as seen on the real-time image display of the system.

As further used herein, the safety region is defined by a safety boundary which is calculated by the system or established by the user. As with the treatment region, the safety boundary is calculated or established by the user based upon the virtual "stops" of the needle structure, actual needle structure positions which have been set or adjusted on the treatment probe by the physician, and/or the energy delivery parameters which are input into or set by the system controller. The safety boundary will differ from the treatment boundary in that the safety boundary will be set at a minimum threshold distance beyond the boundary of the tissue treatment region where the risk of damaging tissue is reduced or eliminated entirely.

In an aspect of the present invention, methods for deploying a needle structure in tissue comprise positioning a treatment probe having a deployable needle structure near a surface of the tissue to be treated, for example, adjacent to a uterine wall over the myometrium of a uterus. A real-time image of the tissue may be provided, typically using an imaging transducer such as an ultrasonic array which is carried by the treatment probe, and projected onto a display connected to a controller. The real-time image may include an anatomical feature to be treated, such as a fibroid. At least one of a treatment region and a safety region may be projected onto the real-time image prior to deploying the needle structure. A size and/or a position of a boundary of the treatment region and/or the safety region may then be adjusted on the real-time image still prior to deploying the needle structure. After the boundary(ies) of the treatment region and/or the safety region are properly positioned on the real-time image relative to the anatomy to be treated, the needle structure may be deployed from the treatment probe into the tissue to provide treatment within the projected treatment/safety boundary after the boundary has been adjusted.

The boundary of the treatment region and/or safety region can be moved or adjusted in several ways. First, manual movement of the treatment probe by the physician may cause the real time image of the tissue and anatomy projected on the screen to move relative to the treatment/safety boundary(ies) projected on the screen. Since the position(s) of the treatment and/or safety boundary projected on the screen may depend on the calculated position of the needle structure, it will be appreciated that movement of the treatment probe itself may cause the calculated needle position to move within the real-time image. In addition to such gross movement of the treatment probe in the uterus, the position of the treatment or safety region projected on the real-time image can be adjusted by controls on the treatment probe, e.g. by manually manipulating a joystick or directional pad on the control handle of the treatment probe. The treatment probe may comprise one or more sensors to directly detect the translational position of the slide(s) for the needle/tine(s) and/or the shaft(s) for the needle/tine(s). For example, the needle/tine(s) may be translated using one or more servos which may additionally provide positional information of the needle/tine(s). The position of the needles and tines can thereby be determined and tracked by the system controller and used to calculate the relative position(s) of the treatment and/or safety boundaries.

In other embodiments, the position(s) and size(s) of the treatment and/or safety boundaries may also be adjusted on the controller, display screen, and/or outside of the treatment probe control handle using an appropriate interface, such as a keyboard, joy stick, mouse, touch panel, touch screen, or the like. Once the treatment and/or safety boundaries are properly (virtually) positioned on the screen, the controller can control the deployment of the needle structure on the treatment probe. For example, the controller could position servo motors on the treatment probe to position the needle/tine.

Virtual needle location information can be projected onto the real-time image, such as while the position and/or size of the treatment and/or safety boundaries are being adjusted. For example, the needle location information could comprise a plurality of fiducials or markers which are projected onto the real-time image to indicate the projected positions of the needle tip(s), or other needle position information. In other cases, it would be possible to project complete images of the needle lengths as they would travel through the tissue (but prior to actual deployment). The needle location information would, of course, preferably be updated as the projected target positions are being adjusted and would allow the physician to see where the needle will be after needle deployment. Further, virtual stop(s) for the needle/tine(s) based on the treatment and/or safety boundaries may be displayed to indicate to the user the extent to which the needle/tine(s) should be deployed.

In another aspect of the present invention, a system for treating an anatomical feature in tissue comprises a real-time image display, a treatment probe, and a control handle. The treatment probe may carry a deployable needle structure and an imaging transducer, wherein the transducer is connectable to the real-time image display. A control element on the control handle may be manipulated to control at least one of a position or size of a treatment and/or safety region projected on the real-time image display.

An exemplary needle structure may comprise a needle and a plurality of tines which may be advanced from the needle. The tines may assume a distally diverging pattern as they are advanced from the needle.

The treatment systems may optionally further comprise a controller connectible to the treatment probe for delivering energy to the needle structure. In addition to the control handle, the controller may be configured to allow the user to control the projected treatment size and/or projected safety region size based upon both an energy level to be delivered by the controller.

In a further aspect of the present invention, an imaging and therapeutic delivery system may comprise an imaging component comprising an imaging shaft having a proximal end, a distal end, and an imaging transducer at the distal end. A needle component comprising a needle shaft having a distal end and a proximal end and a needle structure reciprocally disposed on or within the shaft may be configured to removably attach to the imaging shaft with the shafts lying side-by-side with their respective axes in parallel.

In specific examples, the imaging transducer on the imaging shaft may be pivotally attached at the distal end of the imaging shaft, and the distal end of the needle shaft is disposed proximally of the pivotally attached imaging transducer when the needle shaft is attached to the imaging shaft. The needle structure in the needle shaft typically reciprocates distally along the axis of the needle shaft, and the imaging transducer pivots away from the axis of the needle shaft when the needle shaft is attached to the imaging shaft.

The imaging component may further comprise an imaging handle section attached to a proximal end of the imaging shaft, and the needle component may further comprise a needle handle section attached to a proximal end of the needle shaft. In such embodiments, the imaging handle section and needle handle section may typically form a complete handle when the needle shaft is attached to the imaging shaft. The imaging handle section usually has an interior which holds circuitry configured to connect the imaging transducer with an external imaging display and the needle handle section including mechanisms for advancing the tine needle structure, and the imaging handle section usually further comprises mechanisms for pivoting the imaging transducer relative to the imaging shaft.

In a still further aspect of the present invention, a method for deploying a plurality of tines from a needle in tissue comprises providing a real-time image of the tissue, including an anatomical feature to be treated, on a display. The needle may be penetrated into tissue proximate the anatomical feature, typically in a distal direction, and tines are deployed from the needle further into the tissue. As with previous embodiments, the tines typically diverge radially as they are advanced distally from the needle to increase the volume of tissue to be treated. At least one of a treatment boundary and a safety boundary may be projected onto the display in response to the tine deployment. An extent of the tine deployment can be adjusted to change the size and/or shape of the treatment and/or safety boundary which is projected on the display. As indicated by one or more sensors within the treatment probe, the positions of the actual needle and tine deployment may be provided and can be relied on to position and reposition the safety and/or treatment boundaries on the real time image until the physician is satisfied that a subsequent treatment will be both safe and effective using the actually deployed needle and tine configuration. In addition to the actual needle and tine deployment, of course, the projected treatment and/or safety boundaries may also depend on the intended power and time lengths of the treatment in a manner analogous to the projections of the virtual boundaries discussed previously. After an acceptable size and/or safety boundary has been achieved, the treatment may be delivered through the tines. In particular embodiments, deployment of the tines may be tracked via sensors in a needle/tine deployment mechanism on a treatment probe used to deploy the needle and tines. In such cases, penetrating the needle may comprise advancing the needle from the treatment probe which has been penetrated into the tissue. Usually, the extent of needle deployment from the treatment probe will also be relied on in determining the projected safety and/or treatment boundaries on the display.

In still further aspects of the present invention, a system for treating an anatomical feature in tissue comprises a real-time display connected to a controller. The system may project and adjust a size of at least one of a treatment boundary or a safety boundary onto the display. A treatment probe having a deployable needle structure and an imaging transducer may be provided which is connectable to the controller and the display. The treatment probe may carry at least one servo drive motor which may be connected to and driven by the controller and/or a control element on the treatment probe handle. The control element and/or controller may be configured to drive the servo motor to position the needle structure to provide a treatment which may be effective over the region defined by the treatment boundary and which may not extend significantly beyond the safety boundary.

In specific embodiments of the system, the needle structure may comprise a needle and a plurality of tines advanceable from the needle in a distally diverging pattern. The at least one servo motor may comprise a first servo motor which drives the needle and a second servo motor which drives the plurality of tines. The system usually comprises a user interface configured to allow the user to virtually adjust the size and/or a position of the treatment and/or safety boundary on the display. In some instances, as described previously, an interface may be on the treatment probe itself such as control element of the treatment probe handle. In other cases, the interface may comprise a more conventional keyboard, mouse, roller ball, touch screen, voice activation, or the like which is connected to the controller to allow the user to virtually position the needle structure prior to actually positioning the needle structure. In still other embodiments, the treatment probe may comprise servo motors for positioning the needle structure and/or sensors for detecting the extent to which the needle structure has been deployed. In such cases, the user may position the needle structure using the servos (without having generated a virtual projection of the safety and/or treatment boundaries), and observe the projected safety and/or treatment boundaries as they are calculated and projected by the system controller. In all cases, the system can be used to deliver energy or other treatments only after the deployment of the needle structure has been confirmed to meet the requirements of the safety and/or treatment boundaries.

In still further aspects of the present invention, methods for treating tissue are provided. An exemplary tissue treatment method may comprise distinct planning and real-time monitoring steps. In the planning phase, a user may control a displayed, graphical representation of the safety and/or treatment boundaries for ablation. These boundary(ies) may be controlled with any number of input devices such as switches, gestures, voice controls, etc. The target depth of the needle and tine(s) may be established during the planning phase and shown on the display as graphical planning guides. In exemplary embodiments, the boundary(ies) for the safety and/or treatment are controlled via a joystick or directional pad on a handle of the probe. Many of the ablation devices described herein comprise two stages—one stage for needle deployment and one stage for deployment of the tine(s). In many cases, the needle of the ablation device is advanced into the tissue to a desired depth before the tine(s) are deployed, and it may be desirable to maintain the position of the advanced needle so that the desired geometry of the deployed tines is not changed and the graphical guides are not invalidated during treatment. The planning phase may allow the user to trade off a shallow but wider tissue ablation against a deeper and narrower ablation.

During the deployment phase, sensors within the treatment probe may monitor the real-time position of the introducer needle, tine(s), and/or their respective deployment shafts, and the display console may display the position(s) detected and the progress of the deployment. When the deployment of the needle and/or tine(s) matches the planned value, the system can indicate the match to the user, such as by visual, auditory, haptic, or other feedback. In exemplary embodiments, display markers corresponding to the needle and/or tine(s) may be aligned and/or overlap with the graphical planning guides displayed. If the user continues to deploy the needle and/or tine(s) past the planned depth, the system can indicate the error and instruct the user to retract the needle and/or tine(s). For instance, the system may display a visual warning or may indicate the display markers corresponding to the needle and/or tine(s) as being outside of the safety boundary. In many embodiments, the system may link the graphical planning guide with the displayed real-time position of the needle and tine(s) and display the graphical planning guide in response to the detected real-time position of the needle and tine(s). In some embodiments, the system allows the user to input an adjustment to the position sensor(s) which may be retained by the system.

In some embodiments, the planning stage is optionally omitted, and the graphical planning guide(s) can reflects the real-time position of the introducer needle and tine(s). The depth of the graphical planning guide(s) may reflect the depth of the introducer needle deployment, and the size of the graphical planning guide(s) may reflect the electrode deployment. Adjustments to the sensor input may be input by the user.

In some embodiments, the planning and monitoring control switch (e.g., joystick or directional pad (i.e., D-pad)) acts as the user interfacing element to perform functions typically performed by a mouse or keyboard, such as feature or menu selections and cursor drawing.

The treatment probe may comprise one or more sensors to detect a position of one or more of the needle, the tine(s), and/or their respective deployment shafts relative to the device handle. The sensor(s) may be any type of position sensor such as linear potentiometers, magnetic sensors, a LVDT sensor, a pulse encoder, to name a few examples. The sensor(s) may sense motion relative to the introducer needle location, or relative to the treatment probe handle of the device. The same or different type of sensor may be used for the needle, the tine(s), and/or their respective deployment shafts.

In still a further aspect of the present invention, methods for deploying a needle structure in tissue are provided. An exemplary method for deploying a needle structure in tissue may comprise a step of providing a real time image of the tissue including an anatomical feature to be treated on a display connected to a controller. A treatment probe having a deployable needle structure may further be displayed as the treatment probe is positioned near the anatomical feature. In addition, at least one of a treatment region or a safety region may be projected on the real time image. The method may further comprise adjusting at least one of a size or a position of a projected boundary of the projected image of the treatment region and/or safety region on the real time image. Adjusting the size and/or position of the projected boundary may in some instances comprise user adjustment of a first user interface of a handle of the treatment probe. Further, the deployable needle structure may be displayed on the real time image as the needle structure is deployed from the treatment probe. In practicing the method, the needle structure may be positioned relative to the treatment probe and the tissue to provide treatment within the projected boundary after the projected boundary has been adjusted, and the treatment probe may be positioned near the anatomical feature in the tissue. In addition, the needle structure may be deployed from the treatment probe by user adjustment of a second user interface of the handle of the treatment probe. In some embodiments, at least one of the size or the position of the projected boundary is re-adjusted after the needle has been positioned relative to the treatment probe and the tissue to provide treatment.

In some embodiments, the first user interface of the handle of the treatment probe may comprise a joystick or directional pad. Optionally, the parameters associated with the projected boundary may be adjusted by adjusting the joystick or directional pad. For example, adjusting the size and/or position of the projected boundary may comprise adjusting the size of the projected boundary, wherein the size of the projected boundary is adjusted by one or more of having the joystick or directional pad pushed in a first direction to enlarge the projected boundary or having the joystick or directional pad pushed in a second direction opposite the first direction to shrink the projected boundary. As another example, adjusting the size and/or position of the projected boundary may comprise adjusting the position of the projected boundary, wherein the position of the projected boundary is adjusted by one or more of having the joystick or directional pad pushed in a third direction to advance the projected boundary or having the joystick or directional pad pushed in a fourth direction opposite the third direction to retract the projected boundary. Typically, the joystick, directional pad, or other user interface will remain stationary with respect to the handle of the treatment probe as the size and/or position of the projected boundary(ies) is adjusted. Alternatively or in addition, a position of the projected boundary may be adjusted by manually repositioning the treatment probe relative to the anatomical feature.

In some embodiments, the handle of the treatment probe may further comprise a second user interface for deploying one or more of the needle structure and a plurality of tines able to advance from the needle structure. The second user interface may comprise one or more slider mechanisms of the handle of the treatment probe. An exemplary treatment probe may alternatively or in addition, comprise the plurality of tines able to advance from the needle structure. In such instances, the method may further comprise detecting real-time positions of the plurality of tines as the plurality of tines are deployed and displaying the plurality of tines on the real time image in response to the detected real-time positions. In the methods described herein, projecting the at least one of the treatment region or the safety region on the real time image may comprise projecting one or more tine stop indicators for the plurality of tines on the real time image. The plurality of tines may be advanced so that the virtual representations of the plurality of tines meet the tine stop indicators. In many embodiments, the first user interface of the handle is adjusted to adjust positions of the tine stop indicators after the plurality of tines has been advanced as such. Typically, the one or more tine stop indicators for the plurality of tines are positioned within anatomical feature to be treated. In some embodiments, the method may further comprise driving a servo motor of the treatment probe to deploy the plurality of tines. In some embodiments, displaying the plurality of tines on the real time image may comprise detecting a real time position of the plurality of tines and displaying a virtual representation of the plurality of tines in response to the detected real time position. In such instances, a position of the virtual representation of the plurality of tines may further be updated in real time.

In some embodiments, the method may further comprise delivering energy through the plurality of tines to treat the anatomical feature. In such instances, the method may further comprise controlling at least one of treatment power or treatment time to limit the extent of tissue treatment to within the treatment region and/or safety region. In some embodiments, the method further comprises delivering energy through the needle structure to treat the anatomical feature. In such instances, the method may further comprise controlling at least one of treatment power or treatment time to limit the extent of tissue treatment to within the treatment region and/or safety region. In some embodiments, projecting the at least one of the treatment region or the safety region on the real time image may comprise projecting one or more needle stop indicators for the needle structure on the real time image. The one or more needle stop indicators may be configured to be near or within anatomical feature to be treated. The needle structure may be advanced so that the virtual representation of the needle structure meets the one or more needle stop indicators. The user interface of the handle may be adjusted to adjust positions of the needle stop indicator after the needle structure has been advanced as such. In some embodiments, the method may further comprise driving a servo motor of the treatment probe to deploy the needle structure. In practicing the methods, displaying the needle structure on the real time image may comprise detecting a real time position of the needle structure and displaying a virtual representation of the needle structure in response to the detected real time position. In some embodiments, the method may further comprise updating a position of the virtual representation of the needle structure in real time.

In yet another aspect of the present invention, systems for treating an anatomical feature in tissue may be provided. The system may comprise a treatment probe comprising a handle, a probe body, and a needle structure deployable from the probe body to treat the anatomical feature; and a real-time display coupled to the treatment probe and configured to display a real time image and project the deployed needle structure and at least one of a treatment region or a safety region on the real time image, wherein the handle comprises a first user interface for adjusting one or more of a size or position of one or more boundaries of the at least one of the treatment region or safety region. In many embodiments, a position of the first user interface remains stationary with respect to the handle as the one or more of the size or position of the one or more boundaries are adjusted.

In some embodiments, the treatment probe may comprise a plurality of tines deployable from the needle structure. In such instances, the real-time display may be configured to display a virtual representation of the plurality of tines in response to a detected position of the plurality of tines. Optionally, the treatment probe may comprise one or more sensors for detecting the position of the plurality of tines. In some embodiments, the real-time display of the system may be configured to show one or more tine stop indicators for the plurality of tines. The first user interface of the handle may be configured to be adjusted to re-position the one or more tine stop indicators after the plurality of tines has been deployed so that the virtual representation of the plurality of tines meets the one or more tine stop indicators. Alternatively or in addition, the handle of the treatment probe may further comprise a second user interface for deploying the plurality of tines. In such instances, the second user interface may comprise a slide mechanism.

In some embodiments, the handle of the treatment probe may further comprise a second user interface for deploying the needle structure. In such instances, the second user interface may comprise a slide mechanism. In some embodiments, the treatment probe of the system may comprise a servo to drive the plurality of tines. Alternatively or in addition, the treatment probe may comprise a servo to drive the needle structure. In some embodiments, the real-time display of the system may be configured to display a virtual representation of the needle structure in response to a detected position of the needle structure. In such instances, the treatment probe may comprise one or more sensors for detecting the position of the needle structure. Alternatively or in addition, the real-time display of the system may be configured to show one or more needle stop indicators for the needle structure. In some embodiments, the first user interface of the handle is configured to be adjusted to re-position the needle stop indicators after the needle structure has been deployed so that the virtual representation of the needle structure meets the needle stop indicator. In some embodiments, the first user interface may be configured to adjust one or more of a position or size of a boundary of the treatment region or the safety region. The adjustment may be handled through a variety of means. For example, the first user interface may comprise a joystick or directional pad on the handle of the treatment probe. The joystick or directional pad may be configured to be pushed in a first direction to enlarge the projected boundary, and may be configured to be pushed in a second direction opposite the first direction to shrink the projected boundary. Optionally, the joystick or directional pad may be configured to be pushed in a third direction to advance the projected boundary, and may in some instances be further configured to be pushed in a fourth direction opposite the third direction to retract the projected boundary.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates a distal end of the needle component being connected to a distal end of the imaging component.

DETAILED DESCRIPTION OF THE INVENTION

Figure 1:
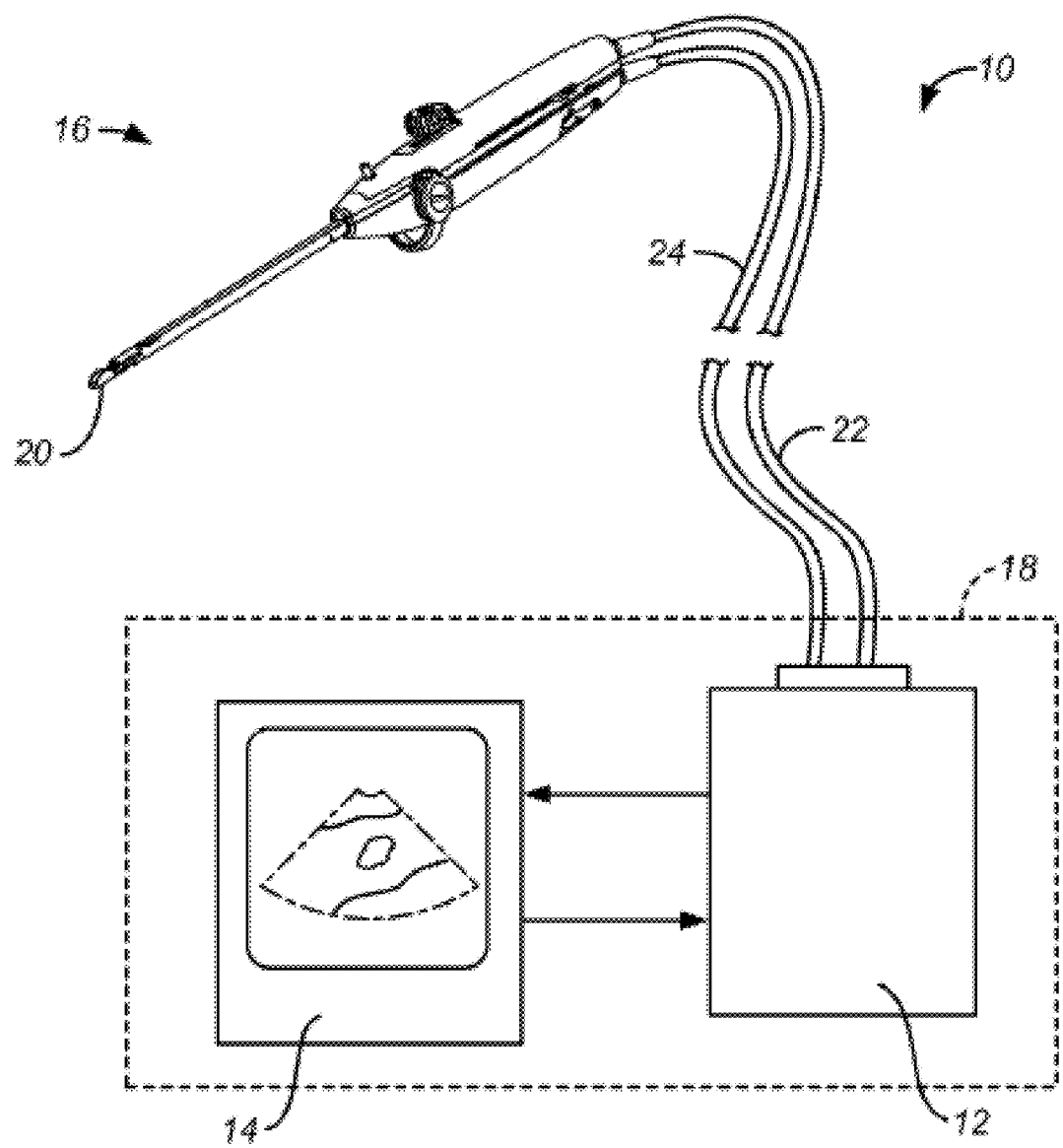
FIG. 1 is a schematic illustration of the system of the present invention comprising a system controller, an image display, and a treatment probe having a deployable needle structure and imaging transducer.

As illustrated in FIG. 1, a system 10 constructed in accordance with the principles of the present invention may include a system controller 12, an imaging display 14, and a treatment probe 16. The system controller 12 will typically be a microprocessor-based controller which allows both treatment parameters and imaging parameters to be set in a conventional manner. The display 14 will usually be included in a common enclosure 18 together with the controller 12, but could be provided in a separate enclosure. The treatment probe 16 may include an imaging transducer 20 which may be connected to the controller 12 by an imaging cord 24. The controller 12 may supply power to the treatment probe 16 via a treatment cord 22. The treatment probe 16 may also be in communication with the controller 12 via the treatment cord 22 such as to provide one or more of a control signal, a feedback signal, a position signal, or a status signal, to name a few. The controller 12 will typically further include an interface for the treating physician to input information to the controller 12, such as a keyboard, touch screen, control panel, mouse, joystick, directional pad (i.e., a D-pad), or the like. Optionally, a touch panel may be part of the imaging display 14. The energy delivered to the treatment probe 16 by the controller 12 may be radiofrequency (RF) energy, microwave energy, a treatment plasma, heat, cold (cryogenic therapy), or any other conventional energy-mediated treatment modality. Alternatively or additionally, the treatment probe 16 could be adapted to deliver drugs or other therapeutic agents to the tissue anatomy to be treated. In some embodiments, probe 16 plugs into an ultrasound system and into a separate radio frequency (RF) generator. An interface line connects the ultrasound system and the RF generator.

Figure 2:
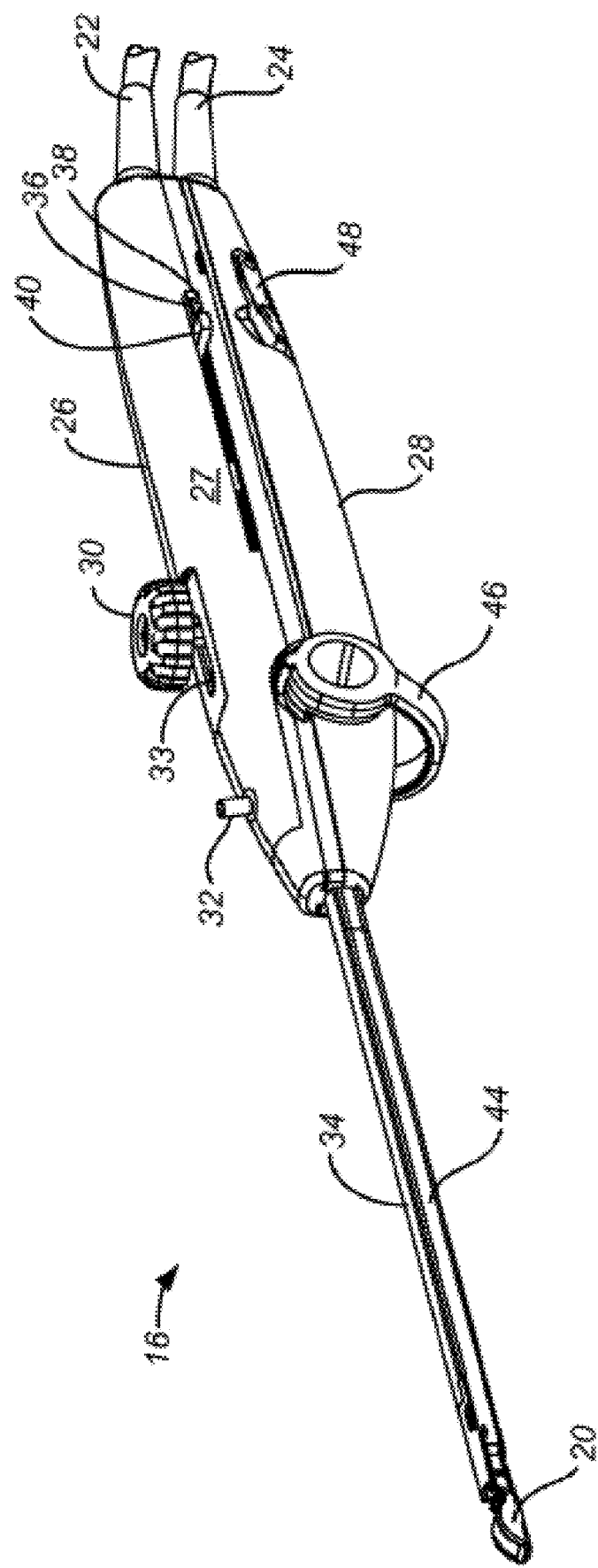
FIG. 2 is a perspective view of the treatment probe of the present invention.
Figure 3:
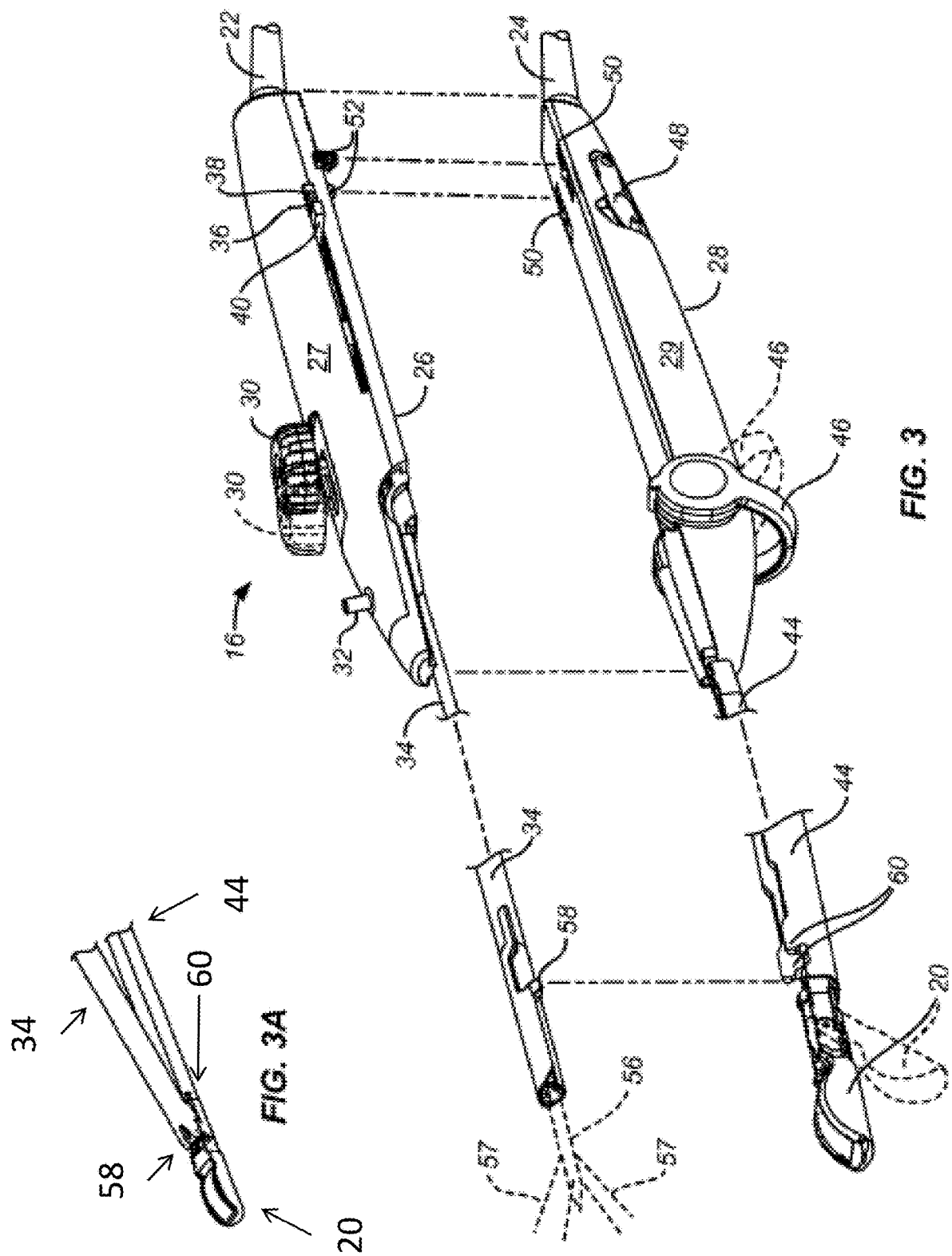
FIG. 3 is a view of the treatment probe of FIG. 2 illustrating an imaging component of the probe separated from a needle component with portions broken away and portions enlarged.

Referring now to FIGS. 2 and 3, the treatment probe 16 may comprise a needle component 26 and an imaging component 28. The needle component 26 and the imaging component 28 may be constructed as separate units or assemblies which may be removably attached to each other for use. After use, the needle component 26 may be separated and will typically be discarded while the imaging component 28 may be sterilized for reuse. The treatment probe 16 is shown in its fully assembled configuration in FIG. 2 and is shown in its disassembled configuration in FIG. 3. In other embodiments of the present invention, the needle component 26 and the imaging component 28 could be combined in a single, integrated handle unit.

The needle component 26 may comprises a handle portion 27 having a control element 30 on its upper surface. The control element 30 may comprise a joystick, a directional pad (i.e., D-pad), or other user interface. While the control element 30 is illustrated as being on the handle portion 27, it is to be understood that it may be located anywhere on the treatment probe 16. For example, the control element 30 may be located anywhere along the handle portion 27 (e.g., near the distal end, the proximal end, or somewhere therebetween). As another example, the control element may be located on a side of the treatment probe (e.g., distally or proximal to the tine slide 40). As another example, the control element may be located on the imaging component 28. Optionally, the control element may face downwards. While particular examples have been given, the control element may be located on any components or elements of the present systems described throughout. For example, the control element may not be located on the treatment probe 16, but may be provided as part of, or be coupled to, the common enclosure 18, controller 12, and/or display. In some instances, the control element may be provided as a stand-alone unit that is coupled to the present systems via wired and/or wireless connections. The control element 30 may be in communication with the controller 12 to adjust the display 14, adjust treatment parameters, adjust the size and/or position of the targeting region and/or the safety region which are shown on the display 14, and/or perform other functions as will be described in more detail below. Optionally, the control element 30 may enable a user to draw marks or lines to identify or document a region of interest (e.g., during a procedure discussed herein). For example, the marks or lines may be made on a displayed image as the control element is manipulated to draw the marks. Optionally, the control element 30 may enable a user to interact with and/or control the controller 12 to access information sources (e.g., MRI images and/or clinical/Artificial Intelligent database) during procedures discussed herein, which may help improve the procedure quality. For example, access of the information sources may be done with menu items described in the present disclosure as the control element is manipulated to navigate the menu items. In some instances, the menu items may accessed on a displayed image as the control element is manipulated to access the information sources (e.g., via the menu items).

The needle 56 may be deployed from the needle shaft 34, and the needle 56 and optional tines 57 together may form a needle structure which may be constructed, for example, as previously described in commonly owned U.S. Pat. Nos. 8,992,427, 8,206,300, and 8,262,574, the full disclosures of which are incorporated herein by reference.

The handle portion 27 of the needle component 26 may further include a fluid injection port 32 which allows saline or other fluids to be injected through the needle shaft 34 into a target region in the tissue being treated, such as the uterus. The needle handle 27 may also include a needle slide 36, a needle release 38, and a tine slide 40 which are used to deploy the needle 56 and tines 57. The needle slide 36 may be slid forward to advance the needle 56 and may be slid backward to retract the needle 56. The tine slide 40 may be slid forward to advance the tines 57 and may be slid backward to retract the tines 57. In some embodiments, the needle 56 and the tines 57 may be coupled to one or more servos within the body of the handle portion 27 which are configured to actuate the needle 57 and the tines 57, and the needle 56 and the tines 57 may be actuated by operating the control element 30 and/or the controller 12. In many embodiments, the needle 56 must be deployed first before the tines 57 can be deployed. The imaging cord 24 may be attachable at a proximal end of the handle portion 27 of the imaging component 28 for connection to the controller 12, as previously described.

The imaging component 28 may comprise a handle portion 29 and an imaging shaft 44. A deflection lever 46 on the handle portion 29 can be retracted in order to downwardly deflect the imaging transducer 20, as shown in broken line in FIG. 3. A needle component release lever 48 may be coupled to a pair of latches 50 which engage hooks 52 on a bottom surface of the handle portion 27 of the needle component 26. The needle component 26 may be releasably attached to the imaging component 28 by first capturing a pair of wings 58 (only one of which is shown in FIG. 3) on the needle shaft 34 beneath hooks 60 on the imaging shaft 44, as shown in FIG. 3A. A bottom surface of the needle handle portion 27 may then be brought down over an upper surface of the imaging handle portion 29 so that the hooks 52 engage the latches 50 to form a complete assembly of the treatment probe 16, where the handle portions together form a complete handle, for use in a procedure. After use, the needle component release lever 48 may be pulled in order to release the hooks 52 from the latches 50, allowing the handle portions 27 and 29 to be separated.

In use, as will be described in more detail below, the control element 30 may be used to both position (translate) and adjust the size of a virtual treatment region which is projected onto the display 14 of the system 10. The control element 30 may be pressed forward (up) and pressed backward (down) in order to translate the position of the treatment/safety region on the image, for example. The control element 30 may be pressed to the left and/or right to adjust the size of the boundary of the treatment/safety region. For example, the control element 30 may be pressed to the left to shrink the boundary while the control element 30 may be pressed to the right to enlarge the boundary. Once the virtual boundaries of the treatment/safety region have been set on the real-time image, the needle and tines may be automatically advanced to the corresponding deployment positions by moving the needle slide 36 and tine slide 40 until their movement is arrested by the user as recommended by the stops. The position of the treatment/safety region may also be dependent on the location at which the physician holds the treatment probe 16 within the target tissue. Thus, advancement of the needle 56 and tines 57 using the slides 36 and 40 will result in the proper placement of the needle and tines within the target tissue only if the treatment probe position is held steady from the time the boundaries are set until advancement of the needle/tines is completed.

In preferred embodiments, the control element 30 may also be manipulated to adjust the length of and/or power delivery during a treatment protocol. For example, the control element 30 may be pressed to select a different control menu from one for the adjustment of the boundaries, and one of the selectable menus may allow the power delivery parameters to be adjusted such as by pressing up/down to adjust the time length for power delivery and pressing left/right to adjust the amount of power delivered. Another menu may comprise a menu for deploying the needle 56 and the tines 57 by operating the control element 30, such as in embodiments where the needle 56 and the tines 57 are articulated using one or more servos within the handle component 27 of the needle component 26. Yet another menu may be selected to allow the control element 30 to move a cursor on the display 14. Thus, the control element 30 may be used to virtually size the treatment/safety region based not only on the degree to which the tines have been advanced, but also the amount of energy which is being delivered to the target tissue.

Optionally, the control element may also be manipulated to make mark ups (e.g., on a display). For example, during a procedure or treatment described herein, a user may utilize the control element 30 to mark, identify, and/or document a region of interest. The marking, identifying, and/or documenting may in some instances be implemented with aid of the display 14. For example the control element 30 may be utilized to mark (e.g., with dots, lines, shapes, circles, polygons, etc) a region of interest that is displayed on the display unit (e.g., in real time during a procedure). Marks made may be saved or recorded in some instances for further use. Optionally, the marking, identifying, or documenting may be implemented by the control element by selecting another menu, substantially as described above. Alternatively, the marking may be available to be implemented by the control unit while having selected a given menu described above as further described below.

Optionally, the control element may also be manipulated to access information sources. The information sources may in some instances be accessed to aid and/or improve the procedures described herein. The information sources may include, but are not limited to magnetic resonance imaging (MRI) images, clinical databases, and/or artificial intelligence databases. For example, during a procedure or treatment described herein, a user may utilize the control element 30 to access an information source. The accessing may in some instances be implemented on the display 14. For example the control element 30 may be utilized to access an information source which may be utilized to display relevant information on the display 14. Optionally, accessing of the information source may implement algorithms that automatically or semi-automatically analyze information on the display to help improve the procedures or treatments described herein. Optionally, the accessing of the information sources may be implemented by the control element by selecting another menu, substantially as described above. Alternatively, the accessing of the information sources may be available to be implemented by the control unit while having selected a given menu described above as further described below.

In some instances, a given menu may be provided (or selected) for the control element 30 to provide a plurality of the functionalities described herein. For example, the control element 30 may provide two, three, four, five, six, seven, eight, nine, ten or more of the functionalities (e.g., position (translate) and adjust the size of a virtual treatment region, adjust the length of and/or power delivery during a treatment protocol, deploy the needle and the tines, move a cursor on the display, make mark ups, access information sources, etc) within a single menu. For example, the control element 30 may comprise various mechanisms (e.g., movable, rotatable, depressible, etc). A first mechanism may control a first functionality while a second mechanism may control a second functionality. For example, moving the control element may position and/or adjust a size of a virtual treatment region while rotation the control element may adjust a length of and/or power delivery during a treatment protocol. As another example, moving the control element may allow movement of a cursory on the display while depressing the control element may allow the control element to draw marks or lines to identify or document a region of interest.

Figure 4:
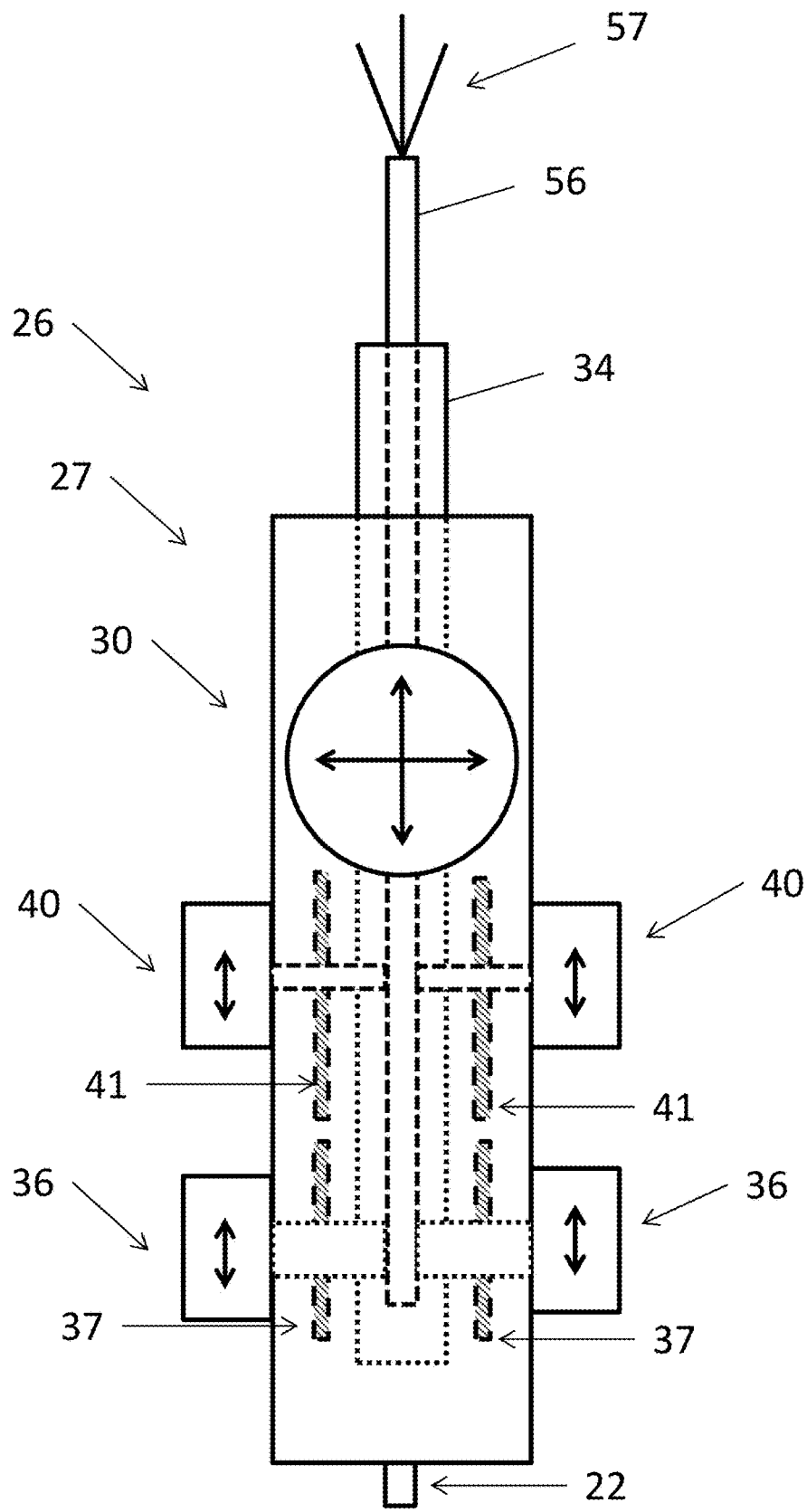
FIG. 4 illustrates a schematic view of the treatment probe of the present invention.

FIG. 4 shows a schematic illustration of the needle component 26 of the treatment probe 16. As shown in FIG. 4, the needle component 26 may comprise one or more needle position sensors 37 and one or more tines position sensors 41. The needle position sensor(s) 37 may be coupled to a handle end portion of the needle deployment shaft 34. Advancement and retraction of the needle 56 by the slide 36 can thereby be tracked by the needle position sensor(s) 37. The needle position sensor(s) 37 may generate a position signal for the needle deployment shaft 34 which may be sent to the controller 12 through the treatment cord 22 and from which the position of the needle 56 can be determined. Likewise, the tines position sensor(s) 41 may be coupled to a handle end portion of the tines deployment shaft disposed within the needle deployment shaft 34. Advancement and retraction of the tines 57 by the slide 40 can thereby be tracked by the needle position sensor(s) 37. The tines position sensor(s) 41 may generate a position signal for the tines deployment shaft which may be sent to the controller 12 through the treatment cord 22 and from which the position of the tines 56 can be determined. The needle position sensor(s) 37 and the tines position sensor(s) 41 may comprise any type of position sensor such as a linear encoder, a linear potentiometer, a magnetic sensor, a linear variable differential transformer (LVDT) sensor, a rheostat sensor, or a pulse encoder, to name a few. The positions of the needle 56 and/or tines 57 may be tracked in real time by the positions sensors 37, 41 and the controller 12. The calculated treatment and/or safety boundaries may be displayed and adjusted on the display unit 14 as the position of the needle 56 and tines 57 are tracked and optionally updated if moved. Alternatively or in combination, the needle 56 and tines 57 may be translated using one or more servo motors which may additionally provide position information for the needle 56 and the tines 57.

The physician may adjust the control element 30 to locate the boundaries of the treatment/safety region as desired to be shown on the visual display 14.

A particular advantage of this method and system is that the physician can manipulate the treatment/safety boundaries over the target anatomy by either moving the boundaries relative to (or within) the real-time image by manipulating (pressing forward/backward, left/right) the control element 30 or moving the entire real-time image with respect to the target anatomy by manipulating the entire treatment probe 16 in order to get the treatment boundary over the tumor and keeping the safety boundary away from sensitive anatomy. So, before the physician advances any needles into the patient tissue, they can confirm in advance using the virtual targeting interface that the ablation will be effective and safe.

Figure 5:
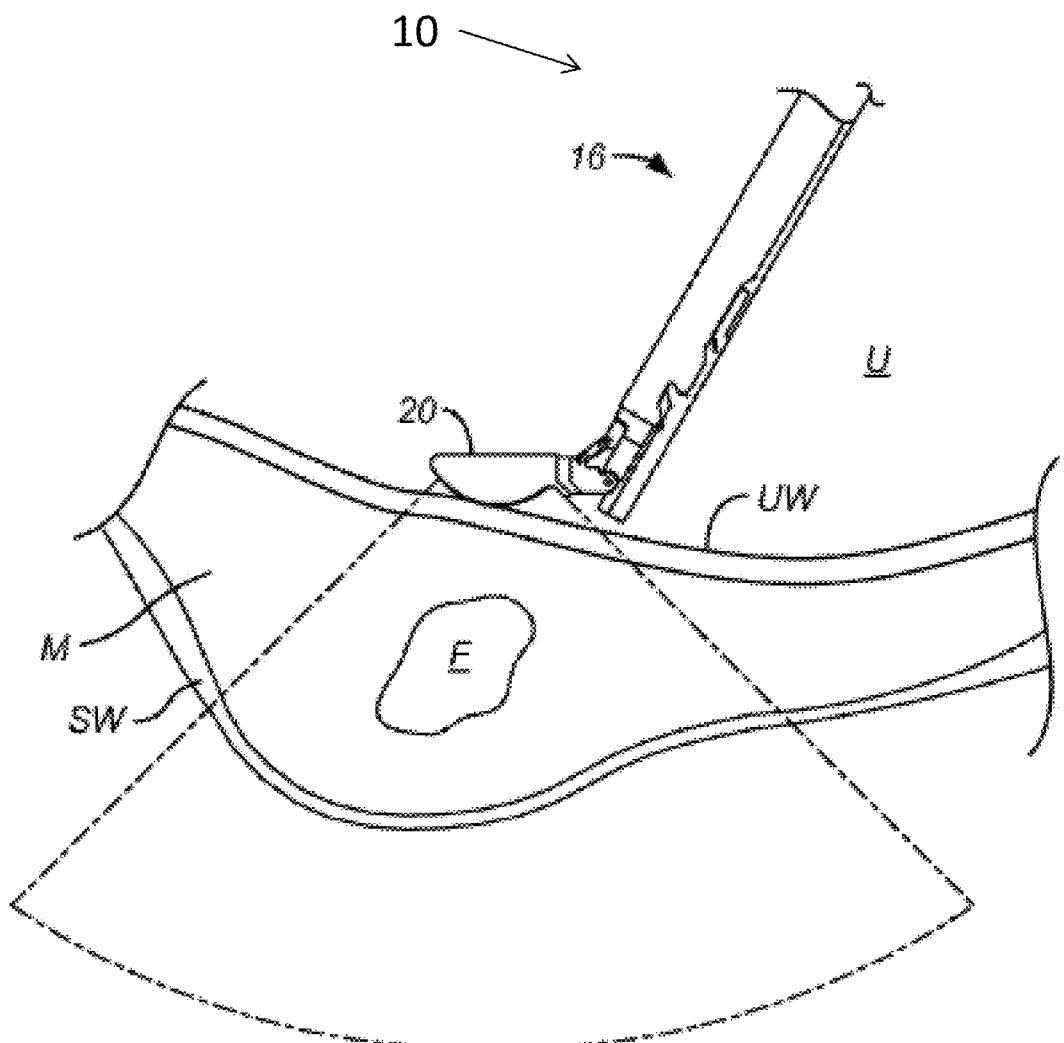
FIG. 5 illustrates a distal portion of the treatment probe introduced into a uterine cavity to image a fibroid in the myometrium.

Referring now to FIG. 5, the system 10 of the present invention can be used to treat a fibroid F located in the myometrium M in a uterus U beneath a uterine wall UW (the endometrium) and surrounded by the serosal wall SW. The treatment probe 16 can be introduced transvaginally and transcervically (or alternately laparoscopically) to the uterus, and the imaging transducer 20 deployed to image the fibroid within a field of view indicated by the broken lines.

Figure 6A:
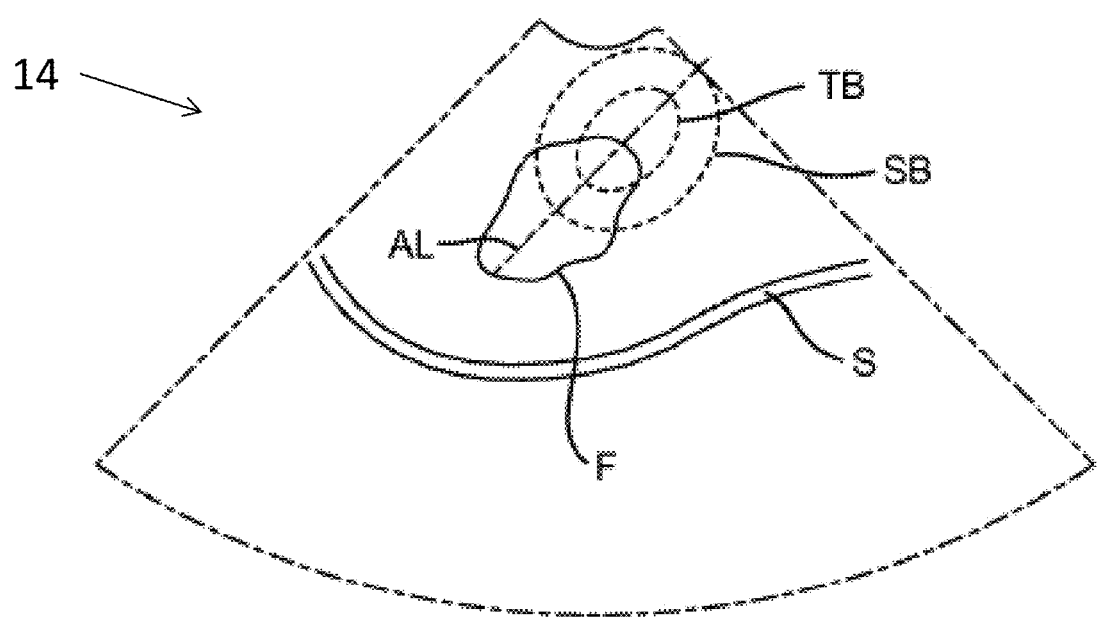
FIGS. 6A, 7A, 8A, 9A, 10A, and 11A illustrate "screenshots" of the real-time image display as the treatment and safety boundaries are being adjusted using the treatment probe in accordance with the principles of the present invention.
Figure 6B:
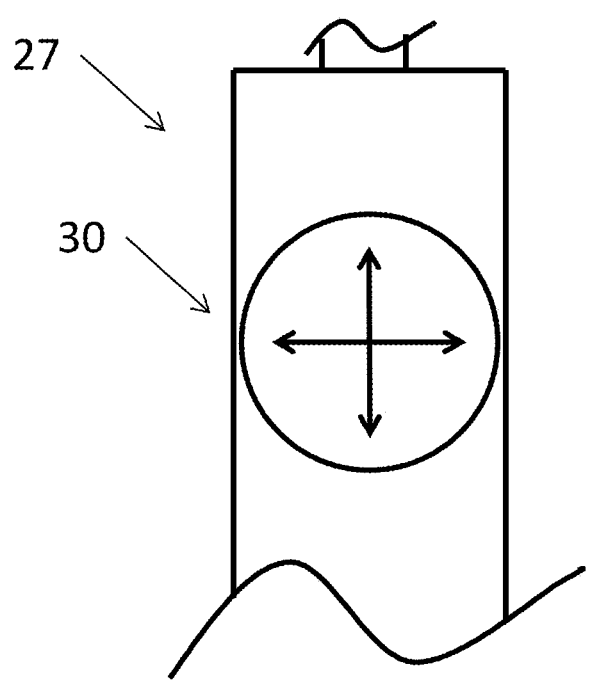
FIGS. 6B, 7B, 8B, 9B, 10B, and 11B illustrate manipulation of the handle which corresponds to the repositioning of the projected images of the treatment and safety boundaries on the real-time images of FIGS. 10A-15A.
Figure 7A:
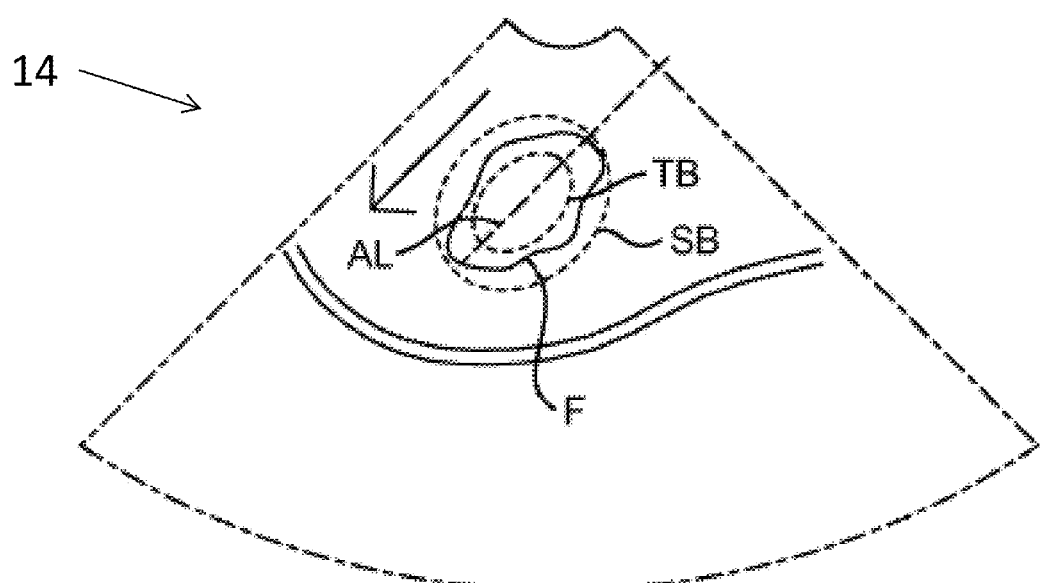
Figure 7B:
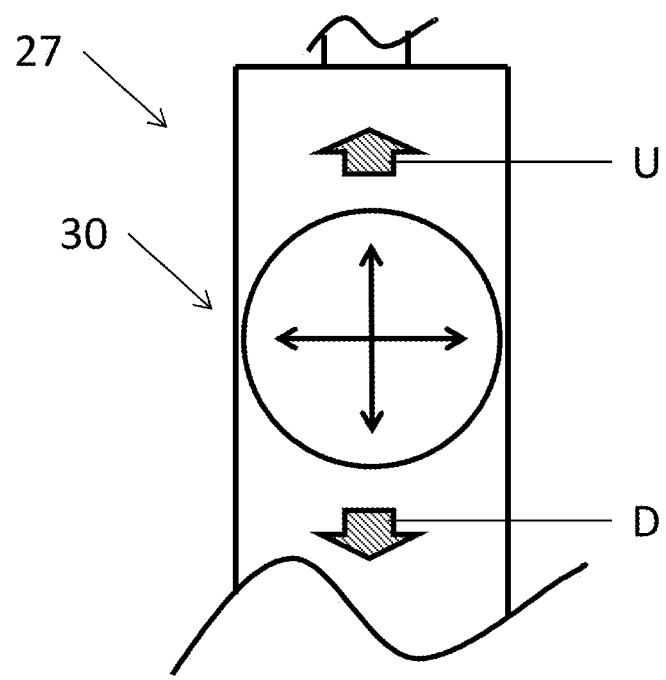

Once the fibroid is located on the display 14, as shown in FIG. 6A, the control element 30 on the handle component 27 can be used to locate and size both a treatment boundary TB and a safety boundary SB. Initially, as shown in FIG. 6A, the virtual boundary lines TB and SB may neither be positioned over the fibroid nor properly sized to treat the fibroid, and the control element 30 may be in a neutral position as shown in FIG. 6B. Prior to actual needle and tine deployment, the physician may want to both position and size the boundaries TB and SB for proper treatment. As the imaging transducer 20 may already be positioned against the uterine wall UW, the only way to advance the treatment and safety boundaries TB and SB is to move the boundaries forward by manipulating the control element 30, such as by pressing the control element 30 forward in the direction of arrow U as shown in FIG. 7B. This manipulation may cause the treatment and safety boundaries TB and SB to move forwardly along the axis line AL. This manipulation may also cause the virtual boundaries on the real-time image display 14 to move over the image of the fibroid, as shown in FIG. 7A. If the treatment and safety boundaries TB and SB need to be retracted, the control element 30 may be manipulated such as by pressing the control element 30 backward in the direction of arrow D as shown in FIG. 7B.

Figure 8A:
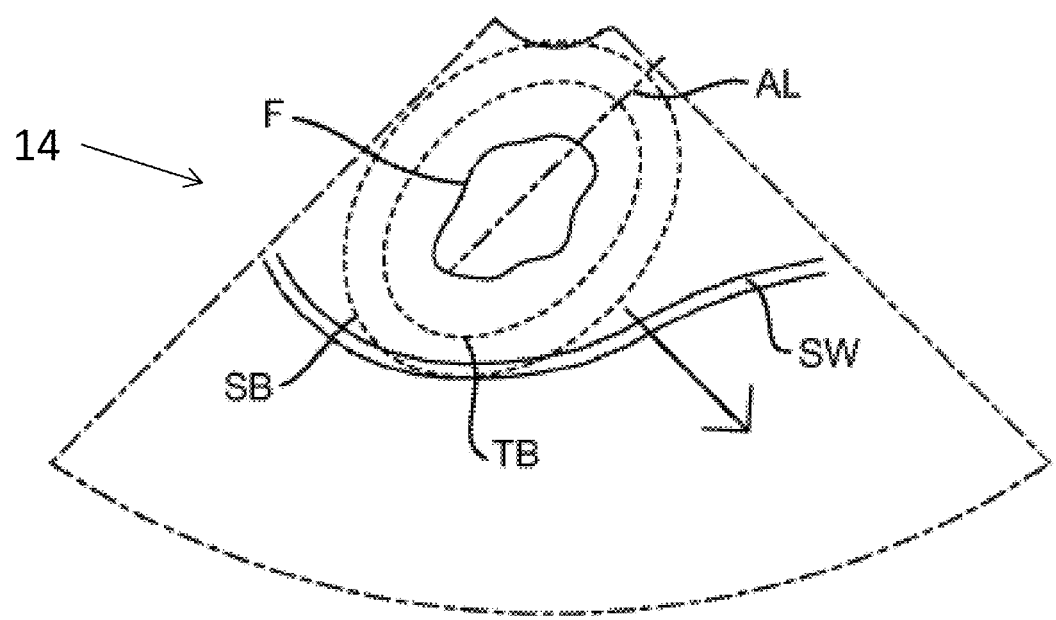
Figure 8B:
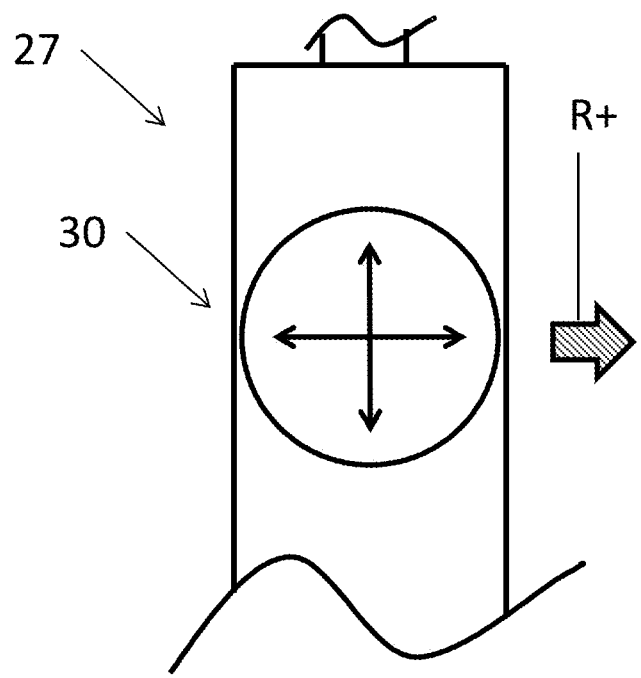
Figure 9A:
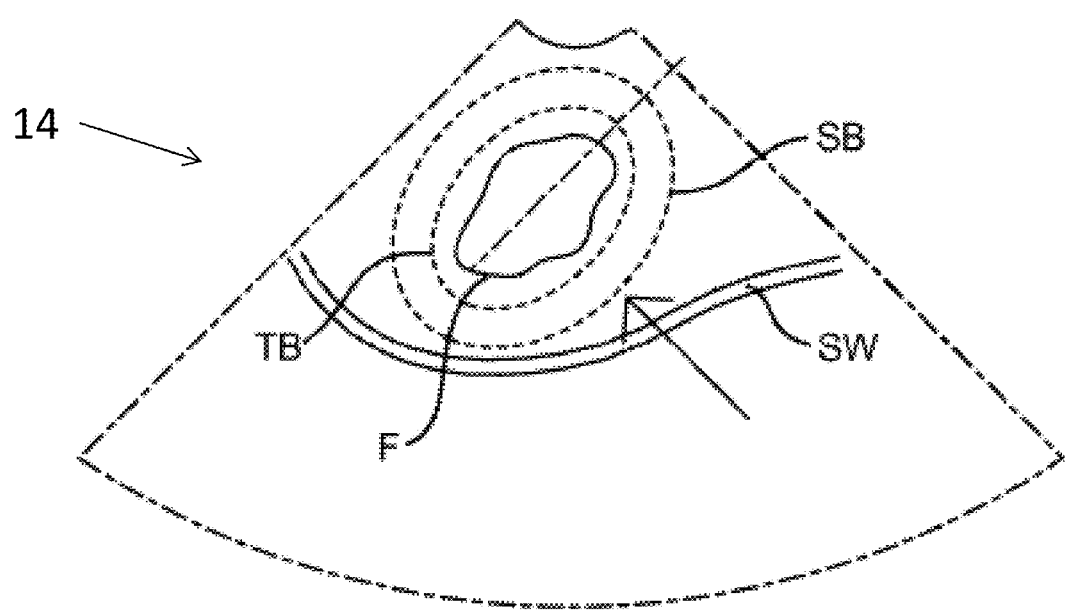
Figure 9B:
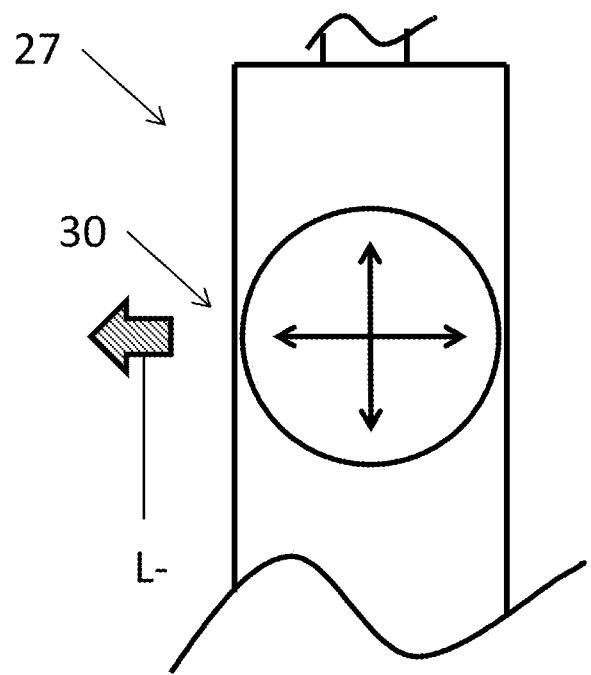

As shown in FIG. 7A, however, the size of the treatment boundary TB may be insufficient to treat the fibroid since the boundary does not extend over the image of the fibroid. Thus, it may be necessary to enlarge the treatment boundary TB by manipulating the control element 30, as shown in FIG. 8B, such as by pressing the control element 30 to the right in the direction of arrow R+. This may enlarge both the treatment boundary TB and the safety boundary SB, as shown in FIG. 8A. While the enlarged virtual treatment boundary TB may now be sufficient to treat the fibroid, the safety boundary SB has extended over the serosal wall SW, as also shown in FIG. 8A. Thus, there may be a risk that the treatment would affect more sensitive tissue surrounding the uterus, and it may be necessary that the virtual safety boundary SB be retracted by again manipulating the control element 30 in an opposite direction, such as by pressing the control element 30 to the left in the direction of arrow L− as shown in FIG. 9B. This manipulation may reduce the size of both the safety and treatment boundaries SB and TB, as shown in FIG. 9A, and the physician may have confirmation that the treatment may be effective because the treatment boundary TB completely surrounds the fibroid on the real-time image display, and that the treatment will be safe because the safety boundary SB is located within the myometrium M and does not cross the serosal wall SW on the real-time image display.

Figure 10A:
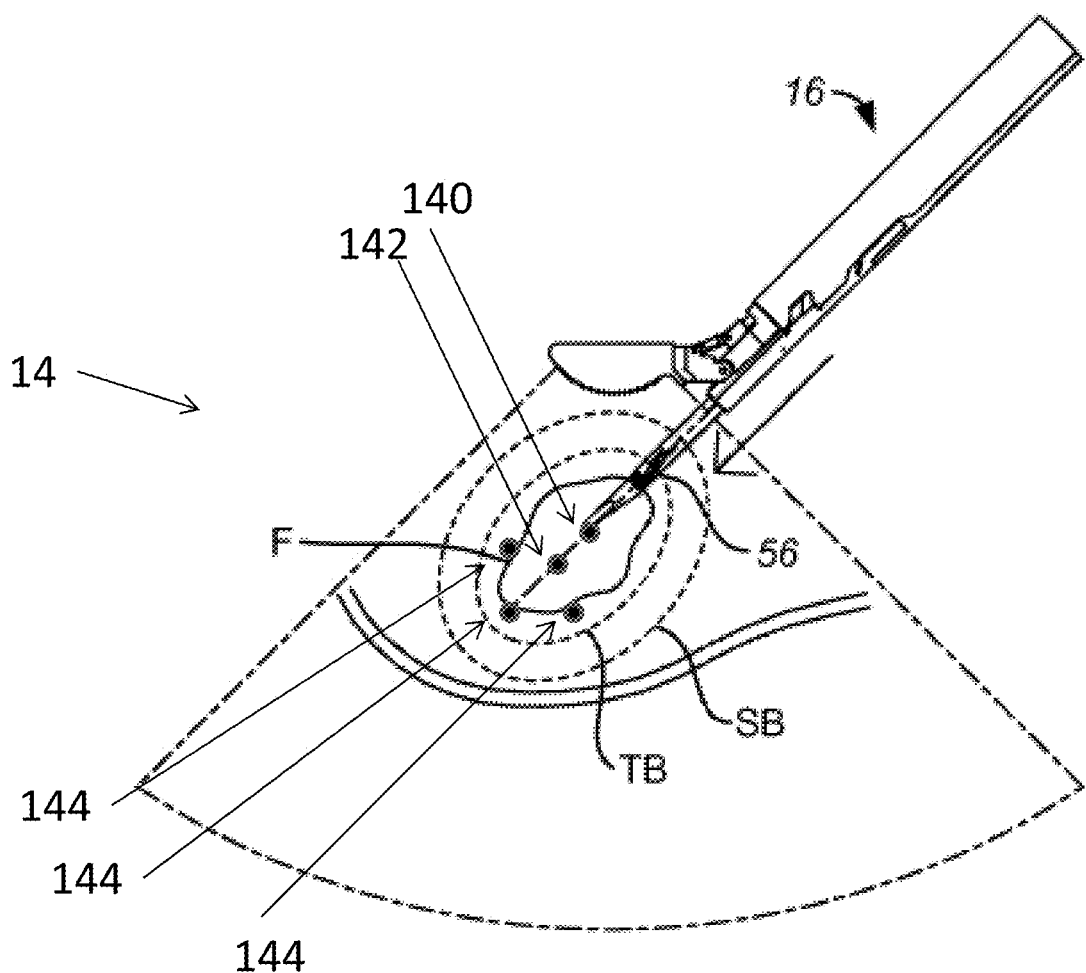
Figure 10B:
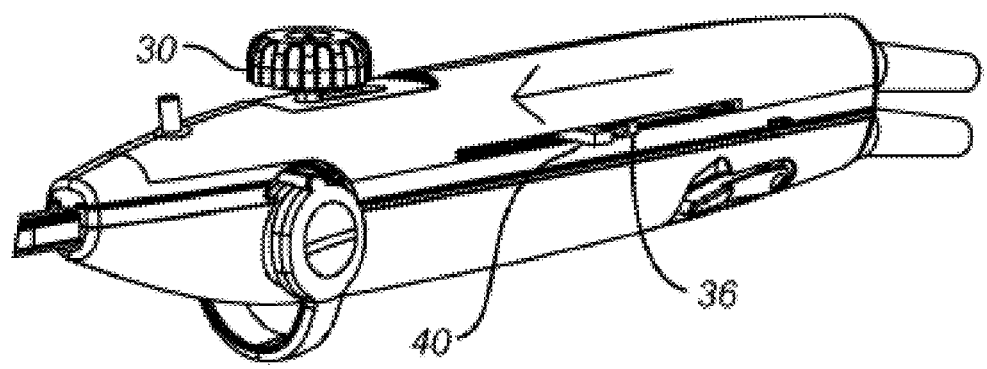

While holding the treatment probe 16 steady, the physician may then advance the needle slide 36, as shown in FIG. 10B, causing the needle 56 to extend into the fibroid F, as shown in FIG. 10A. The illustration in FIG. 10A includes a representation of the treatment probe 16 which may corresponds to the physical probe which is present in the patient. The remainder of FIG. 10A corresponds to the image present on the target display 14. The treatment and safety boundaries TB, SB may determine a virtual stop indicator or fiducial 142 for the needle 56. The target display 14 may include a position indicator 140 for the needle 56, in many cases the tip of the needle 56. In some cases, the positions of the virtual stop indicators or fiducials 142 may correlate with the size and position of the treatment and safety boundaries TB and SB. In other cases, the positions of the virtual stop indicators or fiducials 142 may be adjusted independently with respect to the treatment and safety boundaries TB and SB. The needle 56 may be advanced until the needle position indicator 140 overlaps the stop fiducial 142. In many embodiments, the stop fiducial 142 may be "locked" with the needle position indicator 140 after the overlap occurs. In prior treatment probes, the advancement of the needle structure is halted with a mechanical stop which cannot be adjusted after the needle structure has been fully advanced. In the present invention, stop fiducial 142 is a virtual guide for stoppage of the needle structure and can be further adjusted even after the needle 56 has been advanced to the initial position of the stop fiducial 142.

Figure 11A:
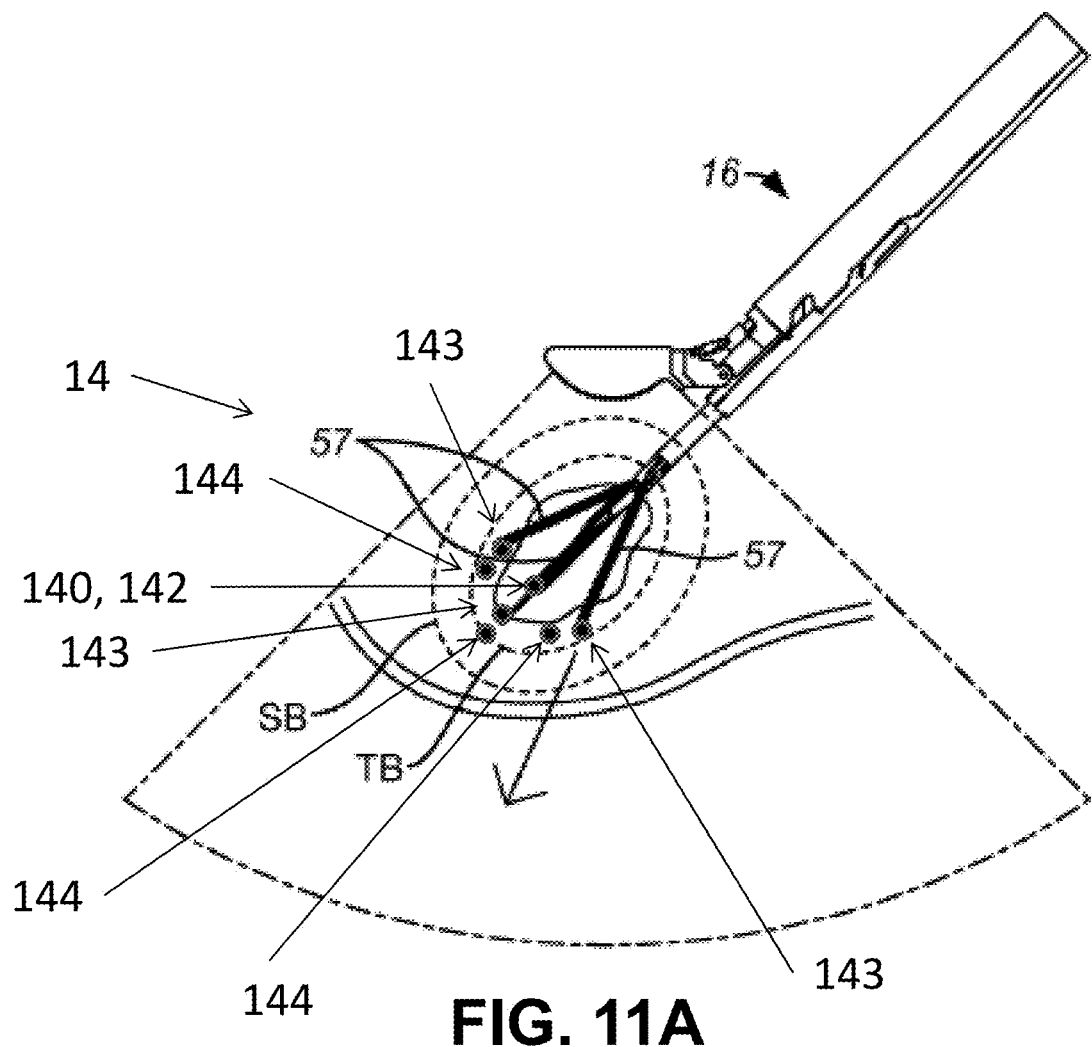
Figure 11B:
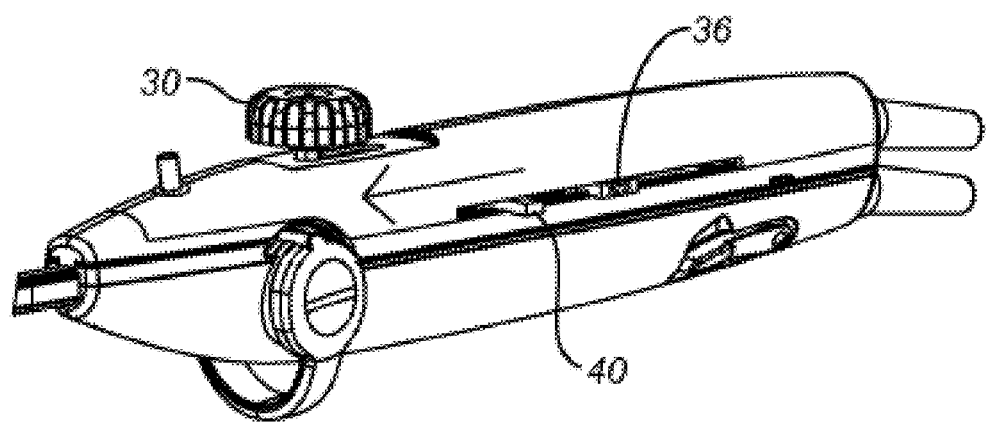

The target display 14 may include a position indicators 144 for the tines 57, in many cases the tip of the tines 56, as shown in FIG. 11A. The treatment and safety boundaries TB and SB may also determine a plurality of virtual stop indicators or fiducials 144 for the tines 57 as shown in FIG. 10A. In many embodiments, the position of the tines may be determined from the needle position sensor 37 to be shown by the tine position indicators 143 on the target display 14 as shown in FIG. 11B. In some cases, the positions of the virtual stop indicators or fiducials 144 may correlate with the size and position of the treatment and safety boundaries TB and SB. In other cases, the positions of the virtual stop indicators or fiducials 144 may be adjusted independently with respect to the treatment and safety boundaries TB and SB. In prior treatment probes, the advancement of the plurality of tines is halted with a mechanical stop which cannot be adjusted after the plurality of tines has been fully advanced. In the present invention, stop fiducials 144 are virtual guides for stoppage of the plurality of tines and can be further adjusted even after the plurality of tines 57 have been advanced to the initial positions of the stop fiducials 144.

After the needle 56 has been fully deployed as indicated by the overlap of the needle position indicator 140 and the stop fiducial 142, the tines 57 may be deployed by advancing the tine slide 40, as shown in FIG. 11B, until the tine position indicators 143 overlap with the stop fiducials 144 for the tines. Optionally, the treatment probe 16 may be rotated about a central axis (typically aligned with the axis of the needle 56) to confirm the treatment and safety boundaries TB, SB in all planes of view about the fibroid. Display 14 may show the position of the treatment and safety boundaries TB and SB in real time relative to the target fibroid F and serosal wall SW. The tines may be configured as shown in FIG. 11A, and power can be supplied to the tines 57 (and optionally the needle 56) in order to achieve treatment within the boundary depicted by the virtual treatment boundary TB. Again, FIG. 11A may mix both the virtual image which would be present on the display 14 as well as the physical presence of the treatment probe 16.

Figure 12A:
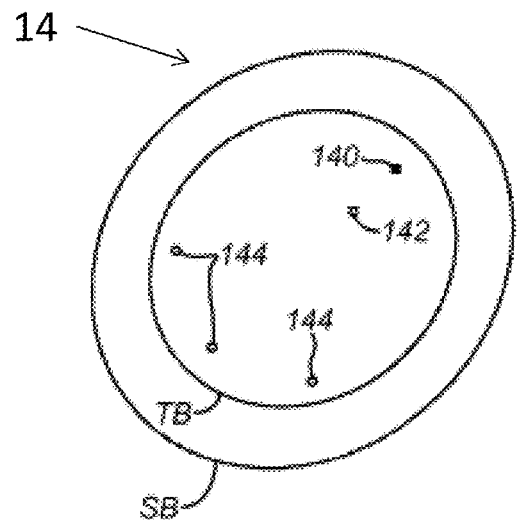
FIGS. 12A, 12B, 12C, and 12D illustrate the provision of fiducials or markers on the real-time image, where the fiducials or markers correspond to needle tip locations.

Referring now to FIG. 12A through 12D, the controller 12 can be programmed to display fiducials or markers on the image display 14, where the fiducials or markers represent particular locations on the "virtual" needle and/or tines. For example, as shown in FIG. 12A, marker 142 may represent a desired position on the needle 56, for example, the location to where a tip of the needle 56 may be intended to advance to and from which the tines are intended to diverge from. An additional marker 140 may be provided which represents the actual tip of the needle 56 in real time. A plurality of additional markers 143 may represent the tips of the tines, as shown in FIG. 11A. The use of such fiducials or markers may help the physician confirm that the actual needle 56 and tines 57 are deployed correctly. The physician should be able to observe the real-time images of the actual needle 56 and tines 57 during deployment, and the associated tips should move until the needle tip reaches marker 142, as indicated by an overlap of markers 140 and 142, and the tine tips hit markers 144, as indicated by an overlap of markers 143 and 144 (or alternatively with the alternative targets 146 and 148 in FIGS. 12B-12D as described below).

Figure 12B:
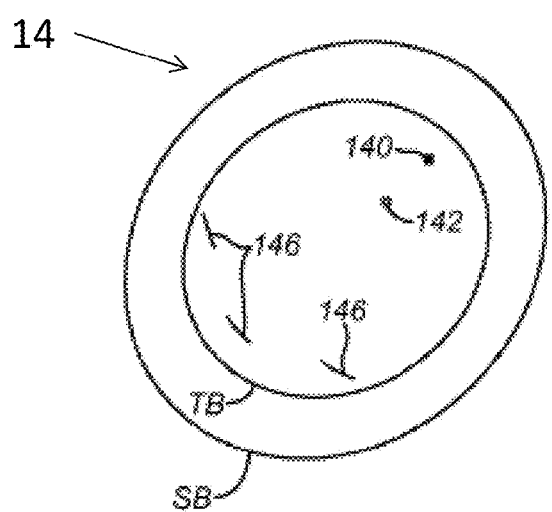
Figure 12C:
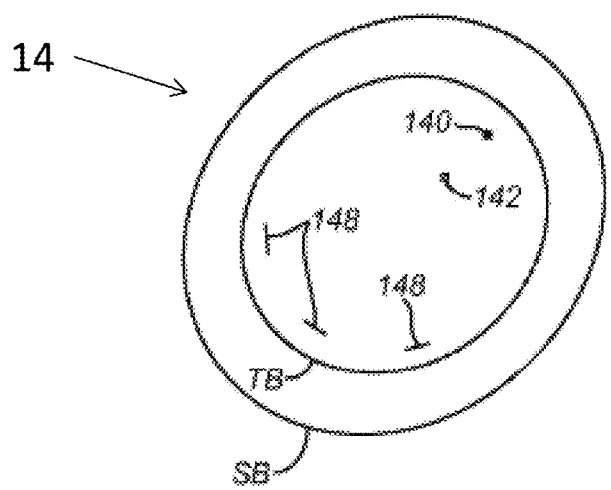
Figure 12D:
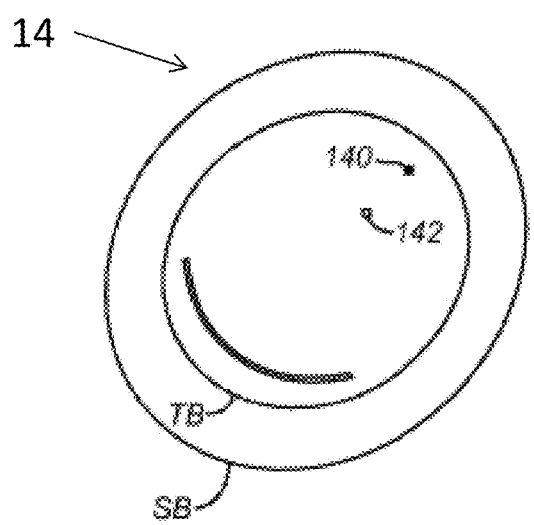

FIG. 12B is similar to FIG. 12A, except that the fiducials representing the tips of the tines 57 are depicted as arcs 146 which represent a range of possible positions for the distal tips of each tine. Such additional information may be useful for the physician when determining both adequacy of treatment and safety risks. As shown in FIG. 12B, each arc has a radius equal to the theoretical electrode deployment length. As shown in FIG. 12C, arcs 148 all have the same radius measured from the origin located at the tip 142. Finally, in FIG. 12D, the arcs of FIG. 12C are joined into a continuous arc which is intended to present a more clear visual presentation for use by the physician.

The physician or other user may virtually position the treatment boundary TB and/or the safety boundary SB on the display screen 14 using an interface other than the control element 30 as described for previous embodiments. For example, the treatment and/or safety boundaries TB and SB may be positioned on a display screen having a real time image of the uterine anatomy using a keyboard, a mouse, a roller ball, a touch screen, voice activation, or any other conventional interface used with computer and other displays. The virtual treatment and/or safety boundaries may be set relative to the actual position of the needle shaft 34 which can be tracked by the system using the image of the shaft in tissue. After the physician is satisfied with the placement of the virtual treatment and/or safety boundaries TB and SB, the physician can then manually advance the needle 56 while the system controller 12 may monitor the advancement through the sensors 37 and 41 in the needle component housing 27. Through visual, audible, or other means, the system can alert the physician when the needle 56 has been advanced by the appropriate distance. After locking the needle, the user can then advance the tines 57 manually while the controller 12 may monitor their position via the sensors 37 and 41. The system may again alert the physician when the tines 57 have been deployed by the appropriate amount within the limits of the virtual treatment and/or safety boundaries TB and SB. The system 12 can then alert the physician that treatment may commence.

Figure 13:
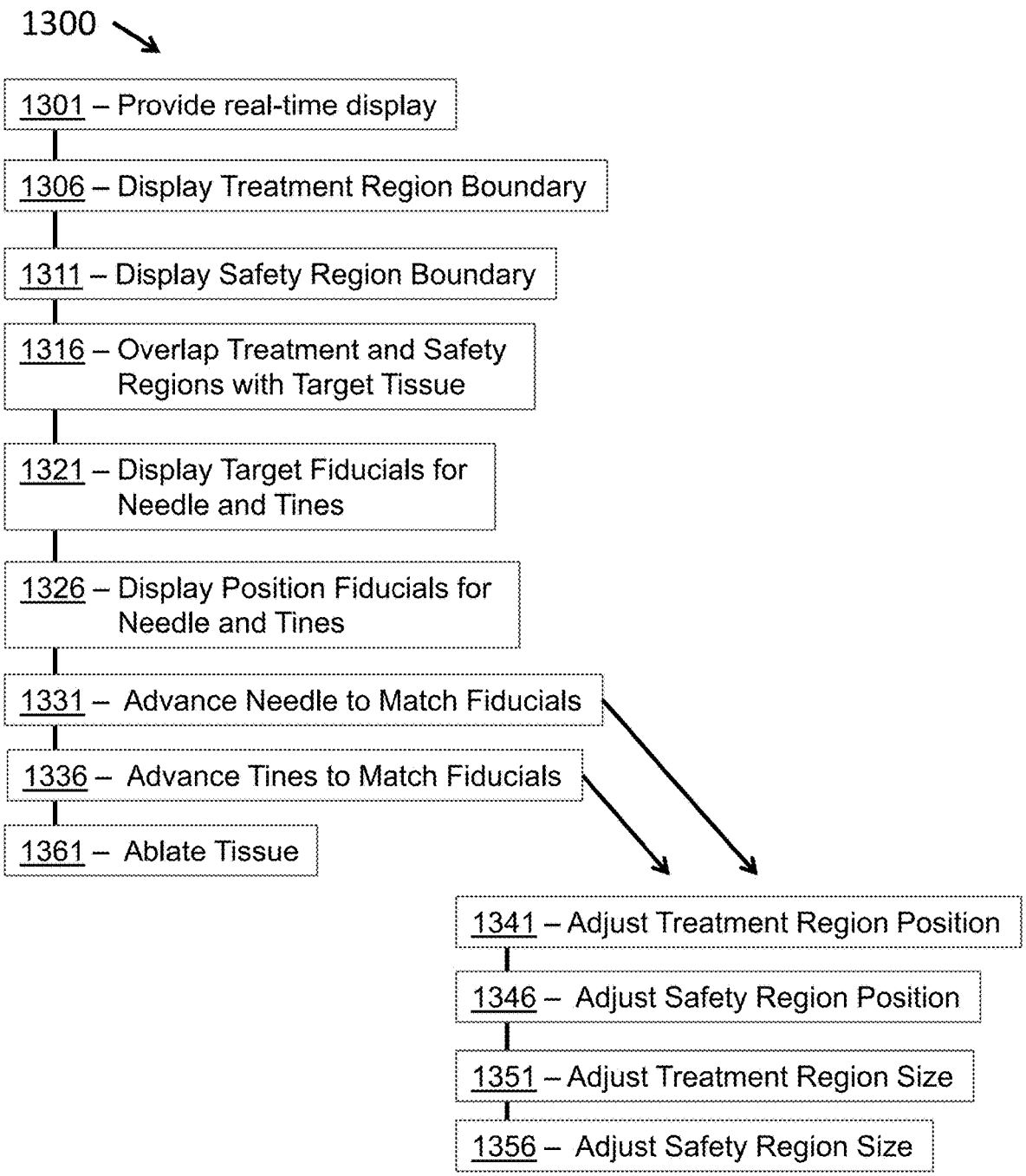
FIG. 13 illustrates a flow chart of a method of treating tissue according to the present invention.

FIG. 13 shows a method 1300 for treating a tissue according to the present invention. The systems and devices described herein may be used to implement the method 1300, including any combination of the steps and sub-steps thereof.

In a step 1301, a real-time display, for example, the display 14 described above, may be provided.

In a step 1306, a treatment region TR may be displayed as described herein.

In a step 1311, a safety region SR may be displayed as described herein.

In a step 1316, the treatment region TR and the safety region SR may be overlapped with the target tissue. For instance, this overlap may be achieved by advancing the treatment probe 16 toward the uterine wall UW and target fibroid F as shown in FIG. 6A.

In a step 1321, target fiducials for the needle and the tines may be displayed, such as on display 14. These target fiducials may be positioned within one or more of the treatment region TR or safety region SR such as described above with respect to FIGS. 10A, 11A, and 12A-12D.

In a step 1331, the needle may be advanced to match its respective target fiducial such as described above with respect to FIG. 10A. Once matched, the user may operate the control element 30 or other user interface to lock the needle position indicating fiducial with the needle target fiducial such that further advancement or retraction of the needle advances or retracts, respectively, the target fiducial as well, as shown on the display. In this manner, the therapeutic target area may be matched to the position of the needle and adjusted accordingly, typically in real-time. Once the needle position indicating fiducial is locked with the needle target fiducial, the size and/or position of the treatment region TR and/or safety region SR may be adjusted in real-time as well.

In a step 1336, the tines may be advanced to match its respective target fiducials such as described above with respect to FIG. 11A. Once the needle position indicating fiducial is locked with the needle target fiducial, the size and/or position of the treatment region TR and/or safety region SR may still be adjusted as well.

In a step 1341, the position of the treatment region TR may be adjusted, such as by manipulating or operating the control element 30 or other user interface as described herein.

In a step 1346, the position of the safety region SR may be adjusted, such as by manipulating or operating the control element 30 or other user interface as described herein.

In a step 1351, the size of the treatment region TR may be adjusted, such as by manipulating or operating the control element 30 or other user interface as described herein.

In a step 1356, the size of the safety region SR may be adjusted, such as by manipulating or operating the control element 30 or other user interface as described herein.

In a step 1361, the target tissue is ablated such as with the treatment probe 16 and when the treatment region TR and safety region SR are sized and positioned as desired and the needle and tines are positioned to their desired positions.

Although the above steps show method 1300 of treating tissue in a patient according to many embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

Figure 14:
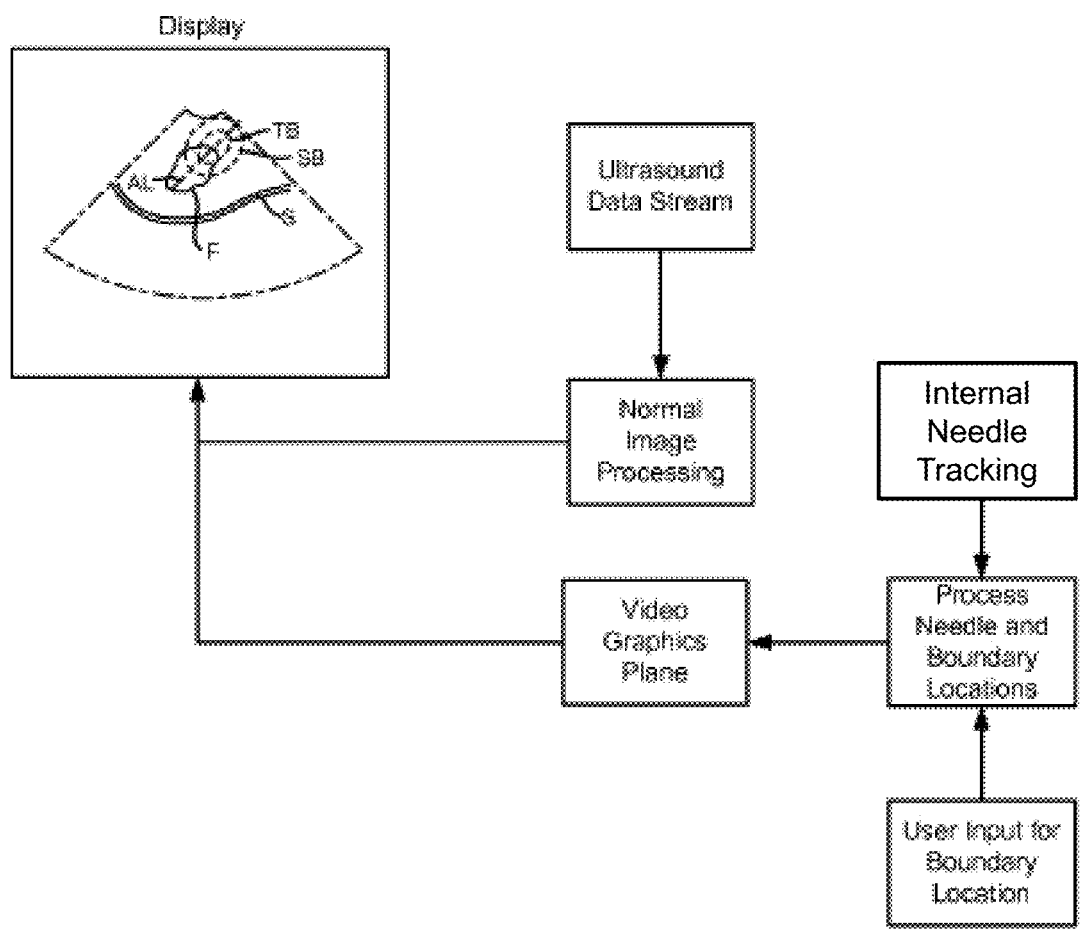
FIG. 14 illustrates a system diagram where needle tracking data is used for tracking the needle position.

Referring now to FIG. 14, the systems and methods of the present invention can rely on internal needle tracking, such as the use of position sensors within the handle component of the needle component of the treatment probe. The position sensors may track and/or determine real-time positions of the needle and the tines in tissue. The real-time data can then be relied on by the system controller to determine whether the needles remain within the boundaries so that both safe and effective treatment can be effected.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for deploying a treatment structure in tissue, said method comprising:
providing a real time image of the tissue including an anatomical feature to be treated on a display connected to a controller;
displaying a probe having a deployable treatment structure as the probe is positioned near the anatomical feature;
projecting an image of at least one of a treatment region or a safety region on the real time image;
adjusting both a size and a position of a projected boundary of the projected image of the treatment region or safety region on the real time image, wherein adjusting both the size and position of the projected boundary comprises user adjustment of a first user interface on a handle of the probe, wherein the first user interface is operable to adjust both the size and position of the projected boundary simultaneously; and
displaying a virtual representation of the deployable treatment structure on the real time image as the treatment structure is deployed from the probe, wherein the treatment structure is positioned relative to the probe and the tissue to provide treatment within the projected boundary after the projected boundary has been adjusted, and
wherein the probe is positioned near the anatomical feature in the tissue and the treatment structure is deployed from the probe by user operation of a second user interface on the handle of the probe, the deployment of the treatment structure from the probe by adjusting the second user interface being independent from the adjustment of the first user interface to adjust the size and position of the projected boundaries.

2. A method as in claim 1, further comprising re-adjusting at least one of the size or the position of the projected boundary after the treatment structure has been positioned relative to the probe and the tissue to provide treatment.

3. A method as in claim 1, wherein a position of the projected boundary is adjusted by manually repositioning the probe relative to the anatomical feature.

4. A method as in claim 1, wherein the first user interface of the handle of the probe comprises a joystick or directional pad.

5. A method as in claim 4, wherein the size of the projected boundary is adjusted by one or more of having the joystick or directional pad pushed in a first direction to enlarge the projected boundary or having the joystick or directional pad pushed in a second direction opposite the first direction to shrink the projected boundary.

6. A method as in claim 5, wherein the joystick or directional pad remains stationary with respect to the handle of the probe as the size and position of the projected boundary are adjusted.

7. A method as in claim 4, wherein the position of the projected boundary is adjusted by one or more of having the joystick or directional pad pushed in a third direction to advance the projected boundary or having the joystick or directional pad pushed in a fourth direction opposite the third direction to retract the projected boundary.

8. A method as in claim 7, wherein the joystick or directional pad remains stationary with respect to the handle of the probe as the size and position of the projected boundary are adjusted.

9. A method as in claim 1, wherein the second user interface on the handle of the probe comprising one or more slider mechanisms coupled to the treatment structure.

10. A method as in claim 1, wherein the treatment structure comprises a needle structure.

11. A method as in claim 10, wherein the treatment probe further comprises a plurality of tines able to advance from the needle structure, and further comprising detecting real-time positions of the plurality of tines as the plurality of tines are deployed and displaying virtual representations of the plurality of tines on the real time image in response to the detected real-time positions.

12. A method as in claim 11, wherein projecting the image of the at least one of the treatment region or the safety region on the real time image comprises projecting one or more recommended tine stop indicators for the plurality of tines on the real time image.

13. A method as in claim 12, further comprising advancing the plurality of tines so that the virtual representations of the plurality of tines are aligned with the recommended tine stop indicators.

14. A method as in claim 13, further comprising adjusting the first user interface of the handle to further adjust positions of the recommended tine stop indicators after the plurality of tines has been advanced so that the virtual representations of the plurality of tines are aligned with the tine stop indicators.

15. A method as in claim 12, wherein the one or more recommended tine stop indicators correspond to one or more recommended stop positions of the tines, and wherein the one or more recommended tine stop indicators for the plurality of tines are configured to be within the anatomical feature to be treated.

16. A method as in claim 11, further comprising driving a servo motor of the treatment probe to deploy the plurality of tines.

17. A method as in claim 11, wherein displaying the plurality of tines on the real time image comprises detecting a real time position of the plurality of tines and displaying a virtual representation of the plurality of tines in response to the detected real time position.

18. A method as in claim 17, further comprising updating a position of the virtual representation of the plurality of tines in real time.

19. A method as in claim 11, further comprising delivering energy through the plurality of tines to treat the anatomical feature.

20. A method as in claim 19, further comprising controlling at least one of treatment power or treatment time to limit an extent of tissue treatment to within at least one of the treatment region or safety region.

21. A method as in claim 1, further comprising delivering energy through the treatment structure to treat the anatomical feature.

22. A method as in claim 21, further comprising controlling at least one of treatment power or treatment time to limit an extent of tissue treatment to within at least one of the treatment region or safety region.

23. A method as in claim 1, further comprising driving a servo motor of the probe to deploy the treatment structure.

24. A method as in claim 1, wherein projecting the image of the at least one of the treatment region or the safety region on the real time image comprises projecting one or more stop position fiducials for the treatment structure on the real time image.

25. A method as in claim 24, wherein the one or more stop position fiducials for the treatment structure are configured to be near or within anatomical feature to be treated.

26. A method as in claim 24, wherein displaying the treatment structure on the real time image comprises detecting a real time position of the treatment structure and displaying the virtual representation of the treatment structure in response to the detected real time position.

27. A method as in claim 26, further comprising updating a position of the virtual representation of the treatment structure in real time.

28. A method as in claim 26, further comprising advancing the treatment structure so that the virtual representation of the treatment structure meets the one or more stop position fiducials for the treatment structure on the real time image.

29. A method as in claim 28, further comprising adjusting the first user interface of the handle to adjust positions of the one or more stop fiducial positions after the treatment structure has been advanced so that the virtual representation of the treatment structure meets the one or more stop position fiducials for the treatment structure on the real time image.

30. A method as in claim 28, further comprising providing visual feedback when the virtual representation of the treatment structure meets the one or more stop position fiducials for the treatment structure on the real time image.

31. A method as in claim 28, further comprising providing auditory feedback when the virtual representation of the treatment structure meets the one or more stop position fiducials for the treatment structure on the real time image.

32. A method as in claim 28, further comprising providing haptic feedback when the virtual representation of the treatment structure meets the one or more stop position fiducials for the treatment structure on the real time image.

33. A method as in claim 1, wherein the handle is free of mechanical stops.

34. A method as in claim 1, further comprising operating the first user interface to select a menu on the display, draw a cursor on the display, move the cursor on the display, draw a mark the image on the display, or draw a line on the display.

* * * * *